US012728037B2

(12) United States Patent
Holland et al.

(10) Patent No.: US 12,728,037 B2
(45) Date of Patent: Sep. 8, 2026

(54) SYSTEM AND METHOD FOR ACCESSING DIFFERENT TISSUE TARGETS OF THE EYE

(71) Applicant: ViaLase, Inc., Aliso Viejo, CA (US)

(72) Inventors: Guy Holland, San Juan Capistrano, CA (US); Tibor Juhasz, San Clemente, CA (US); Reza Khazaeinezhad, Lake Forest, CA (US); Wesley W. Lummis, Rancho Santa Margarita, CA (US); Eric R. Mikula, Aliso Viejo, CA (US); Ferenc Raksi, Mission Viejo, CA (US); Manu Sharma, Ladera Ranch, CA (US); Hadi Srass, Yorba Linda, CA (US); Carlos G. Suarez, Tustin, CA (US)

(73) Assignee: ViaLase, Inc., Aliso Viejo, CA (US)

( * ) Notice: Subject to any disclaimer, the term of this patent is extended or adjusted under 35 U.S.C. 154(b) by 775 days.

(21) Appl. No.: 17/890,094

(22) Filed: Aug. 17, 2022

(65) Prior Publication Data

US 2024/0058169 A1 Feb. 22, 2024

(51) Int. Cl.
*A61F 9/008* (2006.01)

(52) U.S. Cl.
CPC ...... *A61F 9/008* (2013.01); *A61F 2009/0087* (2013.01); *A61F 2009/00872* (2013.01); *A61F 2009/00897* (2013.01)

(58) Field of Classification Search
None
See application file for complete search history.

(56) References Cited

U.S. PATENT DOCUMENTS 4,423,931 A 1/1984 Shapiro
4,568,157 A * 2/1986 Kurwa .................... A61F 9/009 351/159.01

(Continued)

FOREIGN PATENT DOCUMENTS

CN 104382689 B 9/2016
CN 113662507 A 11/2021

(Continued)

OTHER PUBLICATIONS

PCT/US2023/027531. IPRP (Nov. 21, 2024).

(Continued)

*Primary Examiner* — Michael T. Holtzclaw
(74) *Attorney, Agent, or Firm* — LOZA & LOZA, LLP; David S. Sarisky

(57) ABSTRACT

An integrated surgical system for accessing one of a plurality of target volumes of ocular tissue in an eye includes a first optical transmission subsystem optically coupled to receive a first light beam, an optics assembly, and a control system. The optics assembly has an optical axis and is configured to couple to the eye to align its optical axis with the optical axis of the eye. The optics assembly is optically coupled with the first optical transmission subsystem to receive the first light beam along one of a plurality of first input axes and to direct the first light beam to a corresponding one of a plurality of first output axes aligned with a corresponding one of the plurality of target volumes of ocular tissue in the eye. The control system is configured to control the first optical transmission subsystem to direct the first light beam into alignment with a select one of the plurality of first input axes.

48 Claims, 19 Drawing Sheets

(56) References Cited

U.S. PATENT DOCUMENTS 4,664,490 A * 5/1987 Rol .......................... G02C 7/04 351/219
5,123,902 A 6/1992 Müller et al.
5,549,596 A 8/1996 Latina
6,004,314 A 12/1999 Wei et al.
6,033,396 A 3/2000 Huang et al.
6,059,772 A 5/2000 Hsia et al.
6,164,779 A * 12/2000 Volk ........................ A61F 9/009 351/219
6,251,103 B1 6/2001 Berlin
6,482,199 B1 11/2002 Neev
6,525,875 B1 2/2003 Lauer
6,682,523 B2 1/2004 Shadduck
6,989,007 B2 1/2006 Shadduck
7,131,968 B2 11/2006 Bendett et al.
7,192,412 B1 3/2007 Zhou et al.
7,282,046 B2 10/2007 Simon
7,351,241 B2 4/2008 Bendett et al.
7,771,417 B2 8/2010 Telfair et al.
8,011,504 B1 9/2011 Farberov
8,171,937 B2 5/2012 Bendett et al.
8,230,866 B2 7/2012 Hauger et al.
8,394,084 B2 3/2013 Palankar et al.
8,523,926 B2 9/2013 Neev
8,540,659 B2 9/2013 Berlin
8,568,393 B2 10/2013 Palanker
8,585,686 B2 11/2013 Bergt et al.
8,679,089 B2 3/2014 Berlin
8,687,866 B2 4/2014 Marziliano et al.
8,709,001 B2 4/2014 Blumenkranz et al.
8,747,395 B2 6/2014 Rathjen
8,845,624 B2 9/2014 Raksi et al.
8,920,407 B2 12/2014 Raksi et al.
9,028,069 B2 5/2015 Rathjen
9,033,963 B2 5/2015 Vera et al.
9,044,303 B2 6/2015 Kurtz et al.
9,101,448 B2 8/2015 Blumenkranz et al.
9,259,153 B2 2/2016 Goto
9,259,354 B2 2/2016 Horvath et al.
9,265,411 B2 2/2016 Chen et al.
9,271,870 B2 3/2016 Palanker et al.
9,301,878 B2 4/2016 Raksi et al.
9,320,650 B2 4/2016 Bendett et al.
9,441,946 B2 9/2016 Massow et al.
9,456,925 B2 10/2016 Kurtz et al.
9,474,648 B2 10/2016 Palanker et al.
9,498,295 B2 11/2016 Palanker
9,517,006 B2 12/2016 Izatt et al.
9,554,702 B2 1/2017 Papac et al.
9,560,963 B2 2/2017 Buckland et al.
9,603,741 B2 3/2017 Berlin
9,603,744 B2 3/2017 Hailmann et al.
9,629,750 B2 4/2017 Dambacher et al.
9,642,746 B2 5/2017 Berlin
9,681,985 B2 6/2017 Andersen et al.
9,724,238 B2 8/2017 Heitel
9,750,640 B2 9/2017 Palanker et al.
9,820,883 B2 11/2017 Berlin
9,833,357 B2 12/2017 Berlin
9,844,464 B2 12/2017 Bendett et al.
9,936,868 B2 4/2018 Izatt et al.
10,064,757 B2 9/2018 Berlin
10,073,515 B2 9/2018 Awdeh
10,159,600 B2 12/2018 Horvath et al.
10,159,601 B2 12/2018 Berlin
10,165,941 B2 1/2019 Walsh et al.
10,179,066 B2 1/2019 Badawi et al.
10,195,078 B2 2/2019 Horvath et al.
10,195,079 B2 2/2019 Horvath et al.
10,195,080 B2 2/2019 Berlin
10,238,281 B2 3/2019 Isogai et al.
10,238,541 B2 3/2019 Yee et al.
10,292,868 B2 5/2019 Chew et al.
10,335,314 B2 7/2019 Berlin
10,335,315 B2 7/2019 Goldshleger et al.
10,360,683 B2 7/2019 Iwase et al.
10,362,935 B2 7/2019 Dastmalchi et al.
10,362,936 B2 7/2019 Buckland et al.
10,363,169 B2 7/2019 Belkin et al.
10,363,172 B2 7/2019 Kawai et al.
10,383,689 B2 8/2019 Berlin
10,390,883 B2 8/2019 Deladurantaye et al.
10,398,306 B2 9/2019 Liu
10,406,034 B2 9/2019 Siegele
10,426,548 B2 10/2019 Tearney et al.
10,454,237 B2 10/2019 Yu et al.
10,456,030 B2 10/2019 Buckland et al.
10,456,209 B2 10/2019 Peyman
10,478,060 B2 11/2019 Kubota
10,493,274 B2 12/2019 Irazoqui et al.
10,499,809 B2 12/2019 Kalina, Jr. et al.
10,500,094 B2 12/2019 Buzawa et al.
10,517,760 B2 12/2019 Berlin
10,524,822 B2 1/2020 Aljuri et al.
10,537,476 B2 1/2020 Ha et al.
10,542,883 B2 1/2020 Gooi et al.
10,543,122 B2 1/2020 Kahook
10,543,123 B2 1/2020 Neev
10,568,763 B2 2/2020 Vera et al.
10,588,694 B1 3/2020 Neev
10,596,036 B2 3/2020 Pinchuk
10,603,214 B2 3/2020 Bigler et al.
10,603,216 B2 3/2020 Kurtz et al.
10,653,557 B2 5/2020 Rill et al.
10,674,906 B2 6/2020 Kalina, Jr. et al.
10,687,978 B2 6/2020 Berlin
10,702,416 B2 7/2020 Belkin et al.
10,744,033 B2 8/2020 Baerveldt et al.
10,744,034 B2 8/2020 Homer
10,758,418 B2 9/2020 Vold et al.
10,765,559 B2 9/2020 Berlin
10,779,988 B2 9/2020 Fu et al.
10,799,113 B2 10/2020 Vadakke Matham et al.
10,821,023 B2 11/2020 Raksi
10,821,024 B2 11/2020 Raksi
10,888,461 B2 1/2021 Orthaber et al.
10,898,381 B2 1/2021 Bendett et al.
11,019,996 B2 6/2021 Kalina, Jr. et al.
11,019,997 B2 6/2021 Kalina, Jr. et al.
11,026,860 B2 6/2021 Andersen et al.
11,039,958 B2 6/2021 Berlin
11,110,006 B2 9/2021 Raksi
11,147,708 B2 10/2021 Horvath et al.
11,166,630 B2 11/2021 Frisken et al.
11,173,067 B2 11/2021 Raksi
11,246,754 B2 2/2022 Holland et al.
11,278,452 B1 3/2022 Homer
11,316,318 B2 4/2022 Yu et al.
11,376,160 B2 7/2022 Romano et al.
11,382,794 B2 7/2022 Sacks et al.
11,395,765 B2 7/2022 Goldshleger et al.
11,399,981 B2 8/2022 Fu et al.
11,583,445 B2 2/2023 Raksi
11,612,315 B2 3/2023 Delong et al.
11,759,358 B2 9/2023 Dorin et al.
11,771,596 B2 10/2023 Belkin et al.
11,819,457 B2 11/2023 Berlin
11,826,104 B2 11/2023 Kalina, Jr. et al.
11,833,079 B2 12/2023 Kim
11,833,080 B2 12/2023 Hacker et al.
11,850,186 B2 12/2023 Berlin
11,857,463 B2 1/2024 Berlin
11,877,951 B1 1/2024 Junger et al.
2002/0013572 A1 1/2002 Berlin
2004/0070761 A1 4/2004 Horvath et al.
2006/0200113 A1 9/2006 Haffner et al.
2008/0058781 A1 3/2008 Langeweyde et al.
2008/0082078 A1 4/2008 Berlin
2009/0012507 A1 1/2009 Culbertson et al.
2009/0093798 A1 4/2009 Charles
2009/0118718 A1 5/2009 Raksi et al.
2009/0149840 A1 6/2009 Kurtz
2009/0149841 A1 6/2009 Kurtz
2009/0157062 A1 6/2009 Hauger et al.

(56) References Cited

U.S. PATENT DOCUMENTS

2009/0185191 A1 7/2009 Boppart et al.
2010/0130966 A1 5/2010 Brownell
2010/0324543 A1 12/2010 Kurtz et al.
2011/0092965 A1 4/2011 Slatkine et al.
2011/0172649 A1 7/2011 Schuele et al.
2011/0202046 A1 8/2011 Angeley et al.
2011/0213664 A1 9/2011 Osterhout et al.
2011/0214082 A1 9/2011 Osterhout et al.
2011/0282190 A1 11/2011 Caffey et al.
2012/0023557 A1 1/2012 Bevan et al.
2012/0075168 A1 3/2012 Osterhout et al.
2012/0257167 A1 10/2012 Gille et al.
2012/0259321 A1 10/2012 Vera et al.
2012/0283557 A1 11/2012 Berlin
2012/0303007 A1 11/2012 Loesel et al.
2013/0035672 A1 2/2013 Raksi
2013/0085484 A1 4/2013 Van Valen et al.
2013/0103011 A1 4/2013 Grant et al.
2013/0197634 A1 8/2013 Palanker et al.
2013/0226160 A1 8/2013 Rathjen
2013/0237972 A1 9/2013 Raksi
2013/0289450 A1 10/2013 Homer
2014/0128853 A1 5/2014 Angeley et al.
2014/0142599 A1 5/2014 Jeglorz et al.
2014/0176693 A1 6/2014 Podoleanu
2014/0216468 A1 8/2014 Goldshleger et al.
2014/0236066 A1 8/2014 Horvath et al.
2014/0288485 A1 9/2014 Berlin
2014/0354951 A1 12/2014 Zatt et al.
2015/0077528 A1 3/2015 Awdeh
2015/0080783 A1 3/2015 Berlin
2015/0157505 A1 6/2015 Neev
2015/0202083 A1 7/2015 Takeda et al.
2015/0297408 A1 10/2015 Dolzan et al.
2015/0305939 A1 10/2015 Vera et al.
2015/0305940 A1 10/2015 Vera et al.
2015/0313759 A1 11/2015 Vera et al.
2015/0335477 A1 11/2015 Schuele et al.
2015/0359426 A1 12/2015 Buckland et al.
2016/0008169 A1 1/2016 Yu
2016/0095751 A1 4/2016 Berlin
2016/0095752 A1 4/2016 Srinivasan et al.
2016/0213512 A1 7/2016 Palanker et al.
2016/0235586 A1* 8/2016 Fu .......................... A61F 9/009
2016/0367403 A1 12/2016 Siewert et al.
2017/0020732 A1 1/2017 Berlin
2017/0027437 A1 2/2017 Neal et al.
2017/0042736 A9 2/2017 Berlin
2017/0119579 A9 5/2017 Berlin
2017/0127938 A1 5/2017 Izatt et al.
2017/0202708 A1 7/2017 Berlin
2017/0326003 A1 11/2017 Schuele et al.
2018/0028355 A1 2/2018 Raksi
2018/0207029 A1 7/2018 Herekar et al.
2018/0214306 A1* 8/2018 Chassagne ........... A61F 9/0084
2018/0221205 A1 8/2018 Berlin
2018/0235462 A1 8/2018 Gooi et al.
2018/0360310 A1 12/2018 Berlin
2018/0360655 A1 12/2018 Berlin
2019/0021908 A1 1/2019 Scott
2019/0083313 A1 3/2019 Berlin
2019/0083314 A1 3/2019 Berlin
2019/0117459 A1 4/2019 Berlin
2019/0151146 A1 5/2019 Kim
2019/0240070 A1 8/2019 Schmid et al.
2019/0350455 A1 11/2019 Ono
2019/0357768 A1 11/2019 Shareef
2020/0016000 A1 1/2020 Raksi
2020/0016002 A1 1/2020 Raksi
2020/0078216 A1 3/2020 Raksi
2020/0078217 A1 3/2020 Raksi
2020/0078218 A1 3/2020 Holland et al.
2020/0352785 A1 11/2020 Holland et al.
2020/0390605 A1 12/2020 Raksi
2020/0405542 A1 12/2020 Raksi
2021/0022921 A1 1/2021 Berlin
2021/0052416 A1 2/2021 Herekar et al.
2021/0186752 A1 6/2021 Juhasz et al.
2021/0220176 A1 7/2021 Holland et al.
2021/0235986 A1 8/2021 Juhasz et al.
2021/0267799 A1 9/2021 Neal et al.
2021/0298945 A1 9/2021 Juhasz et al.
2021/0307964 A1 10/2021 Holland et al.
2021/0315455 A1 10/2021 Delong et al.
2022/0031503 A1 2/2022 Dorin et al.
2022/0117787 A1 4/2022 Holland et al.
2022/0322932 A1 10/2022 Takaya et al.
2023/0165719 A1 6/2023 Holland et al.
2023/0338191 A1 10/2023 Lörner et al.

FOREIGN PATENT DOCUMENTS

DE 4430720 A1 6/1995
EP 1080706 A1 3/2001
EP 1208792 A1 5/2002
EP 1017308 B1 6/2003
EP 2384727 A1 11/2011
JP 58187911 A 11/1983
JP H06319765 A 11/1994
JP 2001070337 A 3/2001
JP 2005508704 A 4/2005
JP 2013255815 A 12/2013
JP 2015163193 A 9/2015
JP 2016504964 A 2/2016
JP 2016105827 A 6/2016
JP 2016193033 A 11/2016
JP 2019000742 A 1/2019
KR 20180008407 A 1/2018
WO 2010060443 A1 6/2010
WO 2011091326 A1 7/2011
WO 2013188885 A1 12/2013
WO 2017031570 A1 3/2017
WO 2018049246 A1 3/2018
WO 2018073625 A1 4/2018
WO 2018218232 A1 11/2018
WO 2019060756 A1 3/2019
WO 2019173759 A1 9/2019
WO 2020018242 A1 1/2020
WO 2022026239 A1 2/2022

OTHER PUBLICATIONS

Grant, "Tonographic method for measuring the facility and rate of aqueous flow in human eyes". Arch. Ophthalmol. 44(2), pp. 204-214 (1950).

Jones et al., "New methods of measuring the rate of aqueous flow in man with fluorescein". Experimental Eye Research, vol. 5:3, pp. 208-220 (Jul. 1966).

Rosenquist et al., "Ouflow resistance of enucleated human eyes at two different perfusion pressures and different extents of trabeculotomy". Current Eye Research, vol. 8:12, pp. 1233-1240 (1989).

Brubaker, "Goldmann's equation and clinical measures of aqueous dynamics". Experimental Eye Research, vol. 78, Issue 3, pp. 633-637 (2004).

Johnstone, "The aqueous outflow system as a mechanical pump: evidence from examination of tissue and aqueous movement in human and non-human primates". J Glaucoma, vol. 13:5, pp. 421-438 (Oct. 2004).

Dubbelman et al. "The shape of the anterior and posterior surface of the aging human cornea." Vision Research 46 (2006) 9931001. (Jun. 2015).

Hann et al. "Anatomic changes in schlemm's canal and collector channels in normal and primary open-angle glaucoma eyes using low and high perfusion pressures". Glaucoma, vol. 55:9 (Sep. 2014).

Kagemann et al. "Characterisation of Schlemm's canal cross-sectional area." Br J Ophthalmol 2014, 98 (Suppl. II) (Mar. 3, 2014).

McNabb et al. "Complete 360 circumferential gonioscopic optical coherence tomography imaging of the iridocorneal angle." Biomedical Optics Express vol. 6, Issue 4, pp. 1376-1391 (2015).

(56) References Cited

OTHER PUBLICATIONS

Slobodzian et al. "Apples to Apples: Which Camera Technologies Work Best for Beam Profiling Applications, Part 2: Baseline Methods and Mode Effects." Ophir Photonics Group. (2015.

Xin et al. "OCT study of mechanical properties associated with Trabecular meshwork and collector channel motion in human eyes." PLoS One. 2016; 11(9): e0162048. doi: 10.1371/journal.pone.0162048 (Sep. 6, 2016).

Junker et al. "Intraoperative optical coherence tomography and ab interno trabecular meshwork surgery with the trabectome." Clin Ophthalmol. 11: 17551760 (Sep. 28, 2017).

Xin et al. "Aqueous outflow regulation: optical coherence tomography implicates pressure-dependent tissue motion." Experimental Eye Research, vol. 158, pp. 171-186 (May 2017).

PCT/US2023/027531. International Search Report and Written Opinion (Nov. 27, 2023).

Lumibird; "Optimis™ Fusion Next Generation SLY/YAG Laser"; Quantel Medical; Cournon d'Auvergne, France; 2020; 6 pgs.

* cited by examiner 700
702
702a
702b
806
803
707o
804
805
1002b
740b
701b
707i
701b
750b
1001
705
712
710
24
706i
701a
750a
701a
740a
1002a
706o
801
1
800
1000

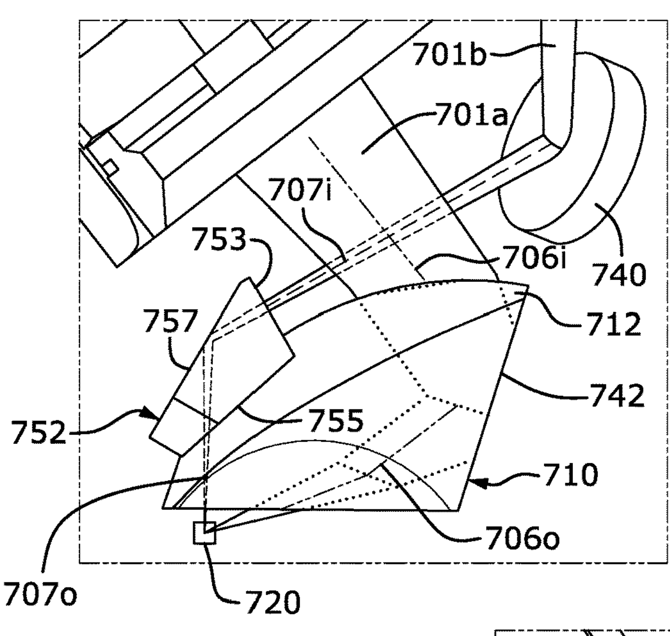
FIG. 8e-1
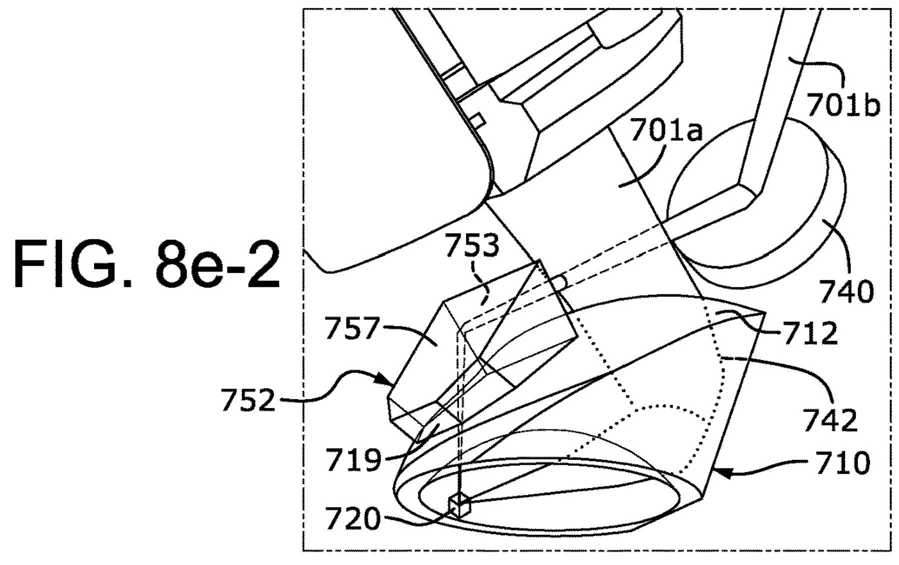
FIG. 8e-2
FIG. 8e-3

810a
700
702
806
803
707o
804
805
707i
701b
752
1002b
701b
753
1001
705
1002a
701a
710
755
24
701a
706i
811
1
742
706o
801
800
1000

1000
700
810a
702
806
803
804
805
707o
707i
1002b
701b
701b
752
753
1001
705
1002a
701a
701a
710
755
807
24
706i
742
706o
801
1
800

SYSTEM AND METHOD FOR ACCESSING DIFFERENT TISSUE TARGETS OF THE EYE

TECHNICAL FIELD

The present disclosure relates generally to the field of medical devices and treatment of diseases in ophthalmology, and more particularly to systems and methods for accessing different tissue targets in the eye, including the irido-corneal angle, the cornea, the crystalline lens, the posterior capsule of the lens, the anterior capsule of the lens, the vitreous humor, and the retina.

BACKGROUND

Before describing the different types of glaucoma and current diagnosis and treatments options, a brief overview of the anatomy of the eye is provided.

Anatomy of the Eye

With reference to FIG. 1, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. The vitreous humor 10 is located between the crystalline lens 4 and the retina 11. Light entering the eye is optically focused through the cornea 3 and crystalline lens.

Referring to FIG. 2, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and is directed to the center of the entrance pupil. These axes of the eye differ from one another only by a few degrees and fall within a range of what is generally referred to as the direction of view.

Different surgical procedures require access to different target tissues of the eye. For example, in procedures for treating glaucoma, target tissue in the irido-corneal angle may need to be accessed. For other procedures, the cornea, the crystalline lens, the posterior capsule of the lens, the anterior capsule of the lens, the vitreous humor, or the retina may need to be accessed. In known systems, such as disclosed in U.S. Pat. Nos. 8,747,395 and 9,028,069, accessing different target tissues of the eye requires an optics assembly that includes different projecting optics connected mechanically with each other such that different optics may be mechanically rotated into alignment with an optical transmission system.

SUMMARY

The present disclosure relates to an integrated surgical system that for accessing one of a plurality of target volumes of ocular tissue in an eye. The system includes a first optical transmission subsystem optically coupled to receive a first light beam, an optics assembly having an optical axis, and a control system. The optics assembly is configured to couple to the eye to align its optical axis with the optical axis of the eye. The optics assembly is optically coupled with the first optical transmission subsystem to receive the first light beam along one of a plurality of first input axes and to direct the first light beam to a corresponding one of a plurality of first output axes aligned with a corresponding one of the plurality of target volumes of ocular tissue in the eye. The control system is configured to control the first optical transmission subsystem to direct the first light beam into alignment with a select one of the plurality of first input axes.

The present disclosure relates to a method of accessing one of a plurality of target volumes of ocular tissue in an eye. The method includes receiving a first light beam at a first optical transmission subsystem; and directing, by the first optical transmission subsystem, the first light beam to a select one of a plurality of first inputs axes of an optics assembly coupled to the eye, wherein the optics assembly has an optical axis and is configured to couple to the eye to align its optical axis with the optical axis of the eye. The method further includes directing, by the optics assembly, the first light beam along the select one of the plurality of first inputs axes to a corresponding one of a plurality of first output axes of the optics assembly aligned with a corresponding one of the plurality of target volumes of ocular tissue in the eye.

The present disclosure also relates to a focusing objective head configured to couple to a patient interface. The patient interface has a window configured to couple to a cornea of an eye having an optical axis. The focusing objective head includes a first optical transmission subsystem that is optically coupled to receive a first light beam and an optics assembly having an optical axis. The optics assembly is configured to couple to the eye to align its optical axis with the optical axis of the eye. The optics assembly is optically coupled with the first optical transmission subsystem to receive the first light beam along one of a plurality of first input axes and to direct the first light beam to a corresponding one of a plurality of first output axes aligned with a corresponding one of the plurality of target volumes of ocular tissue in the eye. The first optical transmission subsystem is configured to direct the first light beam into alignment with a select one of the plurality of first input axes.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems, apparatuses, and methods will now be presented in the detailed description by way of example, and not by way of limitation, with reference to the accompanying drawings, wherein:

FIGS. 7*a* and 7*b* are schematic illustrations of an embodiment of an integrated surgical system having a focusing objective head with an asymmetric optics assembly coupled to an eye through a patient interface.

FIGS. 8*e*1-8*e*3 are isometric illustrations of an embodiment of an asymmetric optics assembly that may be used in place of the optics assembly of FIG. 7*a*.

DETAILED DESCRIPTION

Figure 1:
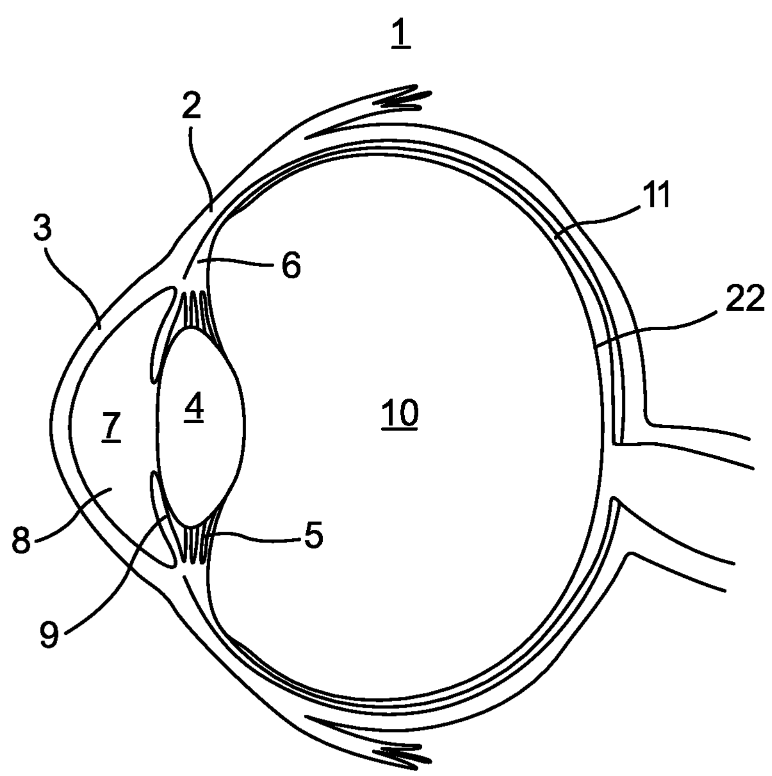
FIG. 1 is a sectional schematic illustration of a human eye and its interior anatomical structures.
Figure 2:
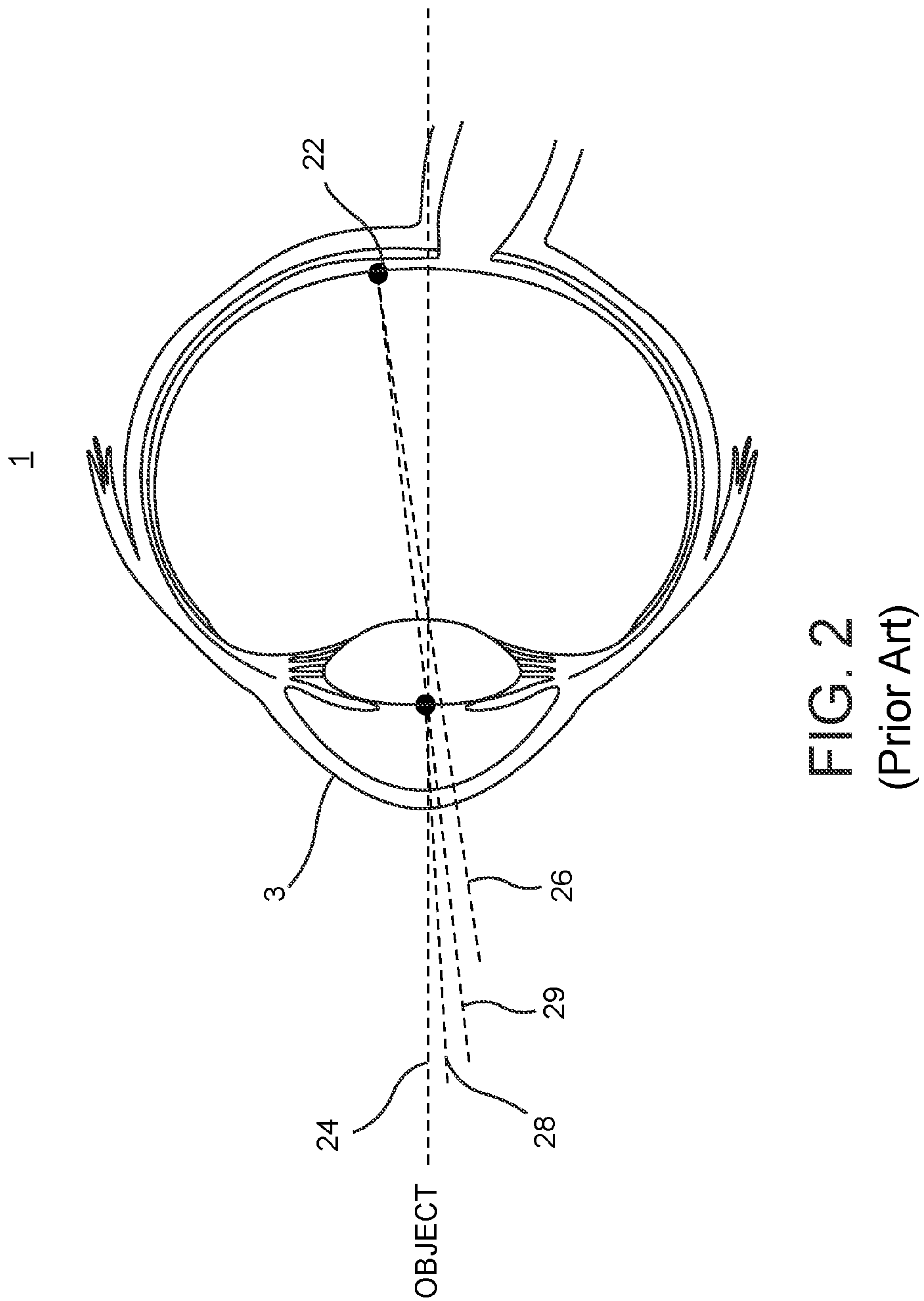
FIG. 2 is a sectional schematic illustration of a human eye showing various axes associated with the eye.

An integrated surgical system disclosed herein is configured to access different tissue targets in the eye through one or more optical transmission subsystems and an optics assembly. Example tissue targets include the irido-corneal angle, the cornea, the crystalline lens, the posterior capsule of the lens, the anterior capsule of the lens, the vitreous humor, and the retina. The optical transmission subsystems are configured to direct light beams into the optics assembly along any one of a number of input axes incident a surface of the optics assembly. To this end, an optical transmission subsystem may include one or more alignment mechanisms, e.g., mechanical actuated flip mirrors, mechanical actuated angular deflectors, fiber optic cables, etc., positioned and oriented relative to the incident surface of the optics assembly and configured to be repositioned and reoriented to direct a light beam into alignment with a select an input axis of the optics assembly. The optics assembly is configured to direct, e.g., reflect, bend, etc., the incident light beam through the optics assembly to an output axis aligned with the tissue target of the eye. In addition to being configured to direct light beams to the optics assembly, the optical transmission system may be further configured to mechanically rotate relative to the optical axis of the eye to enable access to tissue targets around the circumference of the eye. In some configurations, the optics assembly is asymmetric and is mechanically coupled to rotate about the optical axis of the eye together with the optical transmission subsystem. In other configurations, the optics assembly is symmetric and is mechanically coupled to remain in place relative to the eye while the optical transmission subsystem rotates about the optical axis of the eye.

The integrated surgical system disclosed herein enables access to different target tissues of the eye without the need for an optics assembly formed of different optics that requires mechanical rotation to align with an optical transmission system to target appropriate tissue, such as disclosed in U.S. Pat. Nos. 8,747,395 and 9,028,069. In other words, the integrated surgical system disclosed herein accesses different tissue targets in the eye through one or more optical transmission subsystems and an optics assembly having a set, non-reconfigurable optics structure.

Accessing Targets in the Eye

In the following description, the term "beam" may—depending on the context—refer to one of a laser beam, an OCT beam, an illumination beam, a visual observation beam, dual aiming beams, or any other type of light beam. The term "colinear beams" refers to two or more different beams that are combined by optics of the integrated surgical system to share a same path to a same target location of the eye as they enter the eye. The term "non-colinear beams" refers to two or more different beams that have different paths into the eye. The term "co-targeted beams" refers to two or more different beams that have different paths into the eye but that target a same location of the eye. In colinear beams, the different beams may be combined to share a same path into the eye by dichroic or polarization beam splitters, and delivered along a same optical path through a multiplexed delivery of the different beams. In non-colinear beams, the different beams are delivered into the eye along different optical paths that are separated spatially or by an angle between them. In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye. The proximal direction refers to a direction away from the eye.

Figure 3:
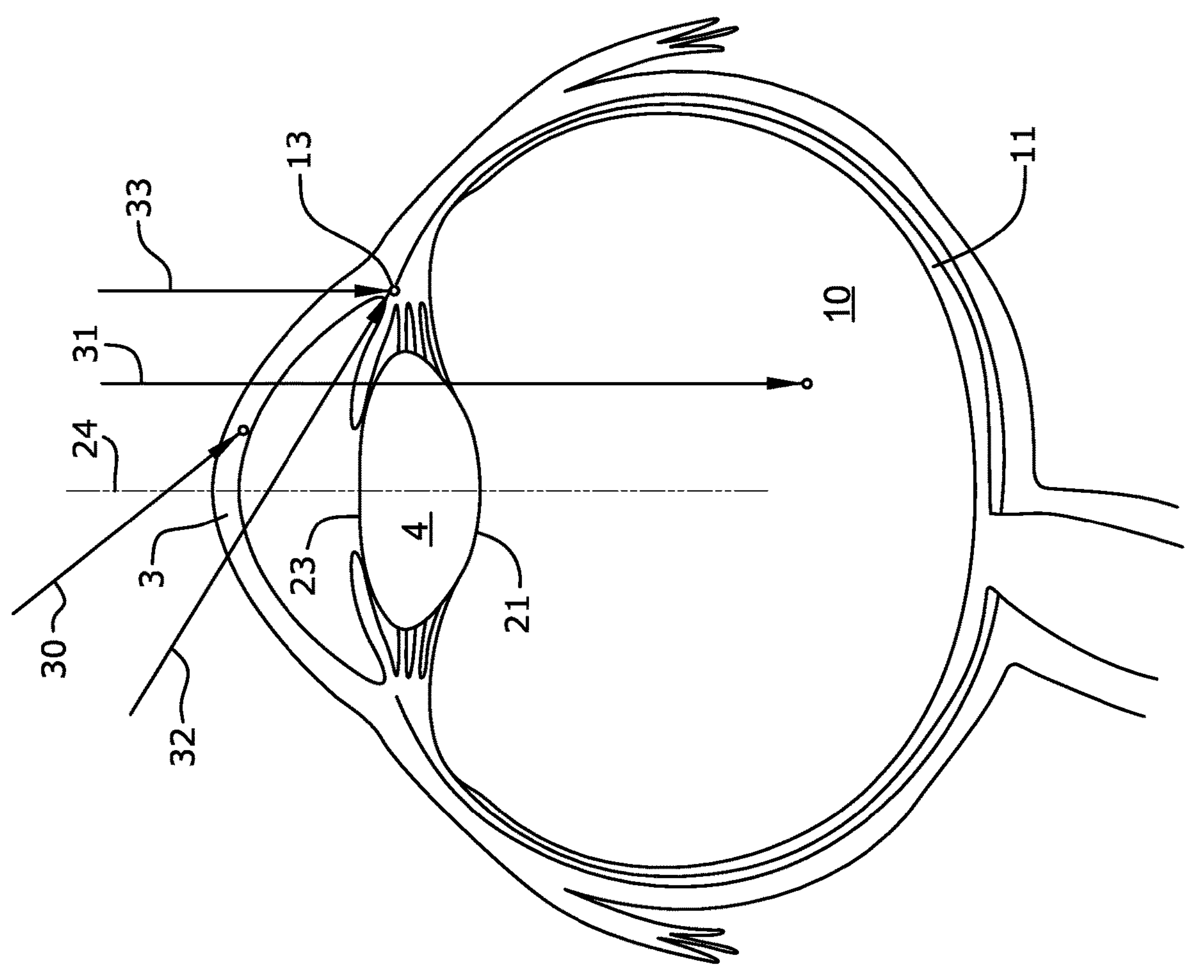
FIG. 3 is a sectional schematic illustration of light-beam paths to different tissue targets of the eye provided by an integrated surgical system for ophthalmic surgery disclosed herein.

With reference to FIG. 3, a feature provided by the integrated surgical system disclosed herein is access to a different tissue targets in the eye through one or more optical transmission subsystems and an integrated optics assembly that does not require mechanical alignment of different optics with an optical transmission system to access different tissue targets—as disclosed in U.S. Pat. Nos. 8,747,395 and 9,028,069. Integrated in this context means the optics assembly is either a singular optic or a combination of multiple optics secured together and fixed in place relative to each other. Different tissue targets accessible by the integrated surgical system disclosed herein include, for example, the irido-corneal angle 13, the cornea 3, the crystalline lens 4, the posterior capsule 21 of the lens, the anterior capsule 23 of the lens, the vitreous humor 10, and the retina 11.

In some embodiments, a tissue target may be accessed by one or more lights beams along a single beam path. For example, one or more of a laser beam, an imaging beam, and a visual observation beam may access the cornea 3 along a first beam path 30. Given the angular arrangement of the first beam path 30 relative to the optical axis 24 of the eye, the first beam path may be referred to as an angled beam path. In another example, one or more of a laser beam, an imaging beam, and a visual observation beam may access the vitreous humor 10 along a second beam path 31 that is substantially parallel relative to the optical axis 24 of the eye. Given this alignment of the second beam path 31, it may be referred to as a parallel beam path. Substantially parallel means within 20 degrees of parallel. In some embodiments, a target may be accessed by different light beams along different, non-colinear beam paths 32, 33. For example, the irido-corneal angle 13 of the eye may be accessed by one or more beams along an angled beam path 32 passing through the cornea 3 and through the aqueous humor 8 in the anterior chamber 7, while one or more other beams may access the irido-corneal angle 13 along a parallel beam path 33 passing through the cornea 3 and into the irido-corneal angle 13 of the eye without passing through the aqueous humor 8 in the anterior chamber 7.

Integrated Surgical System

Figure 4:
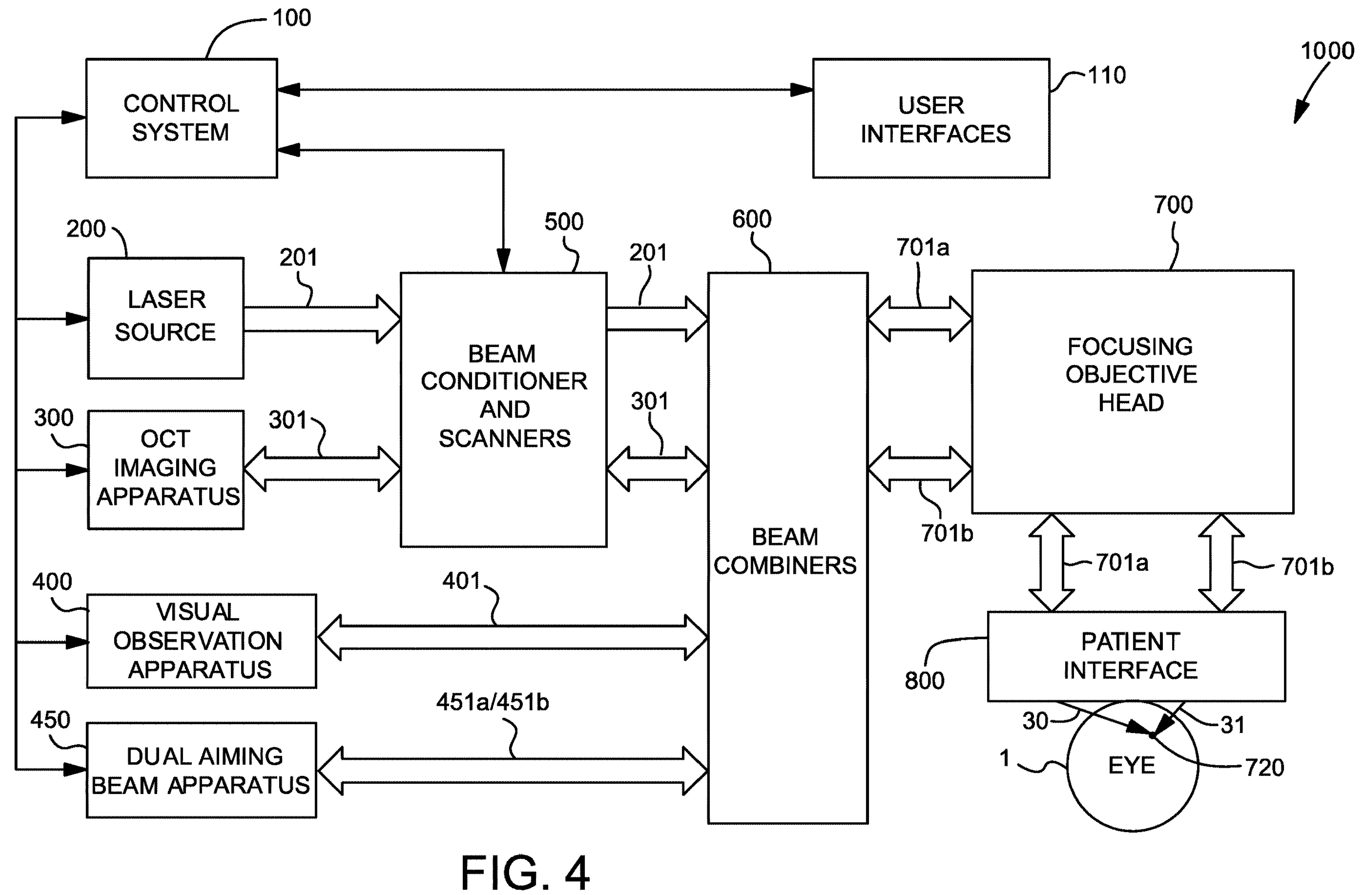
FIG. 4 is a block diagram of an integrated surgical system for ophthalmic surgery.

With reference to FIG. 4, in some embodiments the integrated surgical system 1000 for ophthalmic laser surgery disclosed herein includes a control system 100, one or more user interfaces 110, a surgical component 200, one or more imaging/visual components 300, 400, and a target locating apparatus 450. Other components of the integrated surgical system 1000 include beam conditioners and scanners 500, beam combiners 600, and a focusing objective head 700 that couples with a patient interface 800.

The surgical component 200 may be a femtosecond laser source that outputs a laser beam 201. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

A first imaging/visual component 300 may be an OCT imaging apparatus that outputs an OCT beam 301. OCT technology provides imagery that assist in diagnosing, locating, and guiding laser surgery directed to different tissue targets in the eye. For example, with reference to FIG. 3, OCT imaging may be used to determine the structural and geometrical conditions of the irido-corneal angle 13 and to determine the accessibility of the ocular tissue for treatment. OCT imaging can provide the necessary spatial resolution, tissue penetration and contrast to resolve microscopic details of ocular tissue. When scanned, OCT imaging can provide two-dimensional (2D) cross-sectional images of the ocular tissue. As another aspect of the integrated surgical system, 2D cross-sectional images may be processed and analyzed to determine the size, shape, and location of structures in the eye for surgical targeting. It is also possible to reconstruct three-dimensional (3D) images from a multitude of 2D cross-sectional images but often it is not necessary. Acquiring, analyzing, and displaying 2D images is faster and can still provide all information necessary for precise surgical targeting.

A second imaging/visual component 400 may a visual observation apparatus that outputs a visual observation beam 401 and an illumination source. The visual observation apparatus 400 provides imagery that assist in identifying surgical locations. The visual observation apparatus may include, for example, a video camera and a telescope. The camera may be a digital camera fitted with a goniolens to provide gonioscopic images of the eye. The illumination source is positioned for optimal irradiance of the object of interested, e.g., tissue targets in the eye. Illumination sources may be LEDs or light delivered via fiber optic cables. Illumination schemes are numerous: refractive ballistic schemes where the sources are placed in air and light refracts through the optics to reach the trabecular meshwork; transmissive ballistic schemes where illumination sources are inserted into pre-drilled holes or features inside lenses and adhered using index-matched epoxy; or reflective schemes where light from illumination sources strikes the trabecular meshwork after reflecting off designed reflective surfaces on lenses close to the eye.

The target locating apparatus 450 may be a dual aiming beam apparatus such as disclosed in U.S. Patent Application Publication No. 2021/0235986, title "System and Method for Locating a surface of Ocular Tissue for Glaucoma Surgery Based on Dual Aiming Beams," the contents of which are incorporated herein by reference. The dual aiming beam apparatus 450 outputs a pair of beams of light, referred to herein as dual aiming beams 451*a*/451*b*, for use in detecting a surface of ocular tissue in a surgical field.

The beam conditioner and scanners 500 are configured to set beam parameters of light beams including beam size and divergence. Beam conditioning may also include additional functions, such as setting the beam power or pulse energy and shutter the beam to turn it on or off. As shown in FIG. 4, a laser beam 201 from the femtosecond laser source 200 and an OCT beam 301 from the OCT imaging apparatus 300 are directed towards the beam conditioners and scanners 500. The beam conditioners and scanners 500 include components, e.g., scanning mirrors, for scanning the laser beams 201 and OCT beams 301 independent of each other. Different kind of scanners can be used for the purpose of scanning the laser beam 201 and the OCT beam 301. For scanning transversal to a light beam 201, 301, angular scanning galvanometer scanners are available for example from Cambridge Technology, Bedford, MA, Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective head 700. Therefore, beam conditioners are applied before, after, or in between individual scanners.

The beam combiners 600 are configured to split and combine light beams. The beam combiners 500 may include dichroic or polarization beam splitters that split and recombine light beams with different wavelength and/or polarization. The beam combiner 600 may also include optics to change certain parameters of the individual light beams such as beam size, beam angle and divergence. As shown in FIG. 4, two or more of the laser beam 201, the OCT beam 301, the visual observation beam 401, and the dual aiming beams 451*a*/451*b* may be combined with dichroic, polarization or other kind of beam combiners 600 and provided to the focusing objective head 700 as a combined beam 701 to reach a common target volume of ocular tissue of the eye 1. For example, with reference to FIG. 3, in some embodiments all of these light beams 201, 301, 401, 451*a*/451*b* may be combined to reach a common target along a common beam path 30, 31. In some embodiments different sets of light beams may be combined to reach a common target along different beam paths 30, 31. For example, a first set of beams comprising the laser beam 201, the visual observation beam 401, and the dual aiming beams 451*a*/451*b* may be combined to reach the irido-corneal angle 13 along a first beam path 30, while a second set of beams comprising the OCT beam 301 may reach the irido-corneal angle along a second beam path 31.

Implementation of the functions of the beam conditioners and scanners 500 and beam combiners 600 may happen in a different order than what is indicated in FIG. 4. Specific optical hardware that manipulates the beams to implement those functions can have multiple arrangements with regards to how the optical hardware is arranged. They can be arranged in a way that they manipulate individual light beams separately, in another embodiment one component may combine functions and manipulate different beams. In the embodiment disclosed herein, the beam conditioners and scanners 500 include two sets of scanners, one for scanning the laser beam 201 and the other for scanning the OCT beam 301. Separate beam conditioners within the beam conditioners and scanners 500 set respective beam parameters for the laser beam 201 and the OCT beam 301.

The focusing objective head 700 includes one or more optical transmission subsystems optically coupled to receive one or more light beams 701*a*, 701*b* from the beam combiner 600. Going forward, a light beam identified by reference number 701*a* or 701*b*, may be an individual beam such as a laser beam 201, an OCT beam 301, a visual observation beam 401, dual aiming beams 451*a*/451*b* or any other type of light beam, or a combination of two or more of these individual beams. The focusing objective head 700 also includes an optics assembly. The optical transmission subsystems are configured to direct received light beams 701*a*, 701*b* into alignment with one of a plurality of input axes of the optics assembly. The optical transmission subsystems may be further configured for axial scanning of one or more light beams. The optics assembly is configured to direct a light beam it receives along an input axes to a corresponding output axis that is aligned with one or more tissue targets of the eye. Further details of the optical transmission subsystems and optics assembly are provided below.

The control system 100 is connected to the other components 200, 300, 400, 450, 500, 700 of the integrated surgical system 1000. Control signals from the control system 100 to the femtosecond laser source 200 function to control internal and external operation parameters of the laser source, including for example, power, repetition rate and beam shutter. Control signals from the control system 100 to the OCT imaging apparatus 300 function to control OCT beam parameters, and the acquiring, analyzing, and displaying of OCT images of tissue in the surgical field.

Control signals from the control system 100 to the dual aiming beam apparatus 450 function to control the output of beams of light by the one or more aiming beam sources of the dual aiming beam apparatus. Control signals from the control system 100 to the visual observation apparatus 400 function to control the capturing, image processing and displaying of video images of tissue in the surgical field and spots of light on tissue surfaces in the surgical field that result from the one or more beams of light output by the dual aiming beam apparatus 450. To this end, the line of sight of the visual observation apparatus 400 may be aligned with the femtosecond laser and directed into the target area of the eye.

Control signals from the control system 100 to the beam conditioner and scanners 500 function to control the scanning of a laser beam output by the femtosecond laser source 200 and the scanning of an OCT beam output by the OCT imaging apparatus 300. Control signals to the beam conditioner and scanners 500 may include location, size and shape of surgical patterns expressed in position coordinates of the intended location of focus of the laser and the scanning path of the laser across the surgical volume. These types of control signals can be pre-programmed, with one or more control parameters selectable by the operator. The control parameters of the surgical pattern may include the location of the pattern, the shape, length, width and depth of the pattern, laser spot, line and layer separation and energy of the laser pulses. Control signals to and from various subsystems and components are calibrated prior to operating the surgical system. The calibration includes calibrating the pixel coordinates acquired and displayed by the visual observation apparatus 400 and the OCT imaging apparatus 300 to actual physical coordinates in the eye and includes calibrating commanded motions of the OCT and laser scanner systems to actual OCT and laser beam displacements in the eye.

Control signals from the control system 100 to the focusing objective head 700 may function to control axial scanning of either or both of a laser beam 201 and an OCT beam 301 through a motorized focusing objective. Control signals from the control system 100 to the focusing objective head 700 may also function to control mechanical elements of one or more optical transmission subsystems to thereby direct one or more light beams 701*a*, 701*b* into alignment with an input axis of the optics assembly. Further details of the optical transmission subsystems and optics assembly are provided below.

Commanding the integrated surgical system 1000 to make a surgical incision includes docking the system on the eye, acquiring, and displaying visual observation images including spots from the dual aiming beams, and OCT images on a computer screen, determining the coordinate location and other parameters of the intended surgical incision based on the displayed images and instructing the control system 100 to execute the surgical pattern based on information collected from those images. The parameters based on the images may be determined by the operator of the integrated surgical system 1000 or may be determined by an image processing and analyzing computer algorithm. Instructions using these parameters can be given by the operator as entering input data in the form of text, mouse clicks and drag and drop commands on the computer screen. Alternatively, a system processor that may be included in the control system 100 generates instructions for execution by the control system based on the previously determined parameters.

Single Optical Transmission Subsystem

Figure 5A:
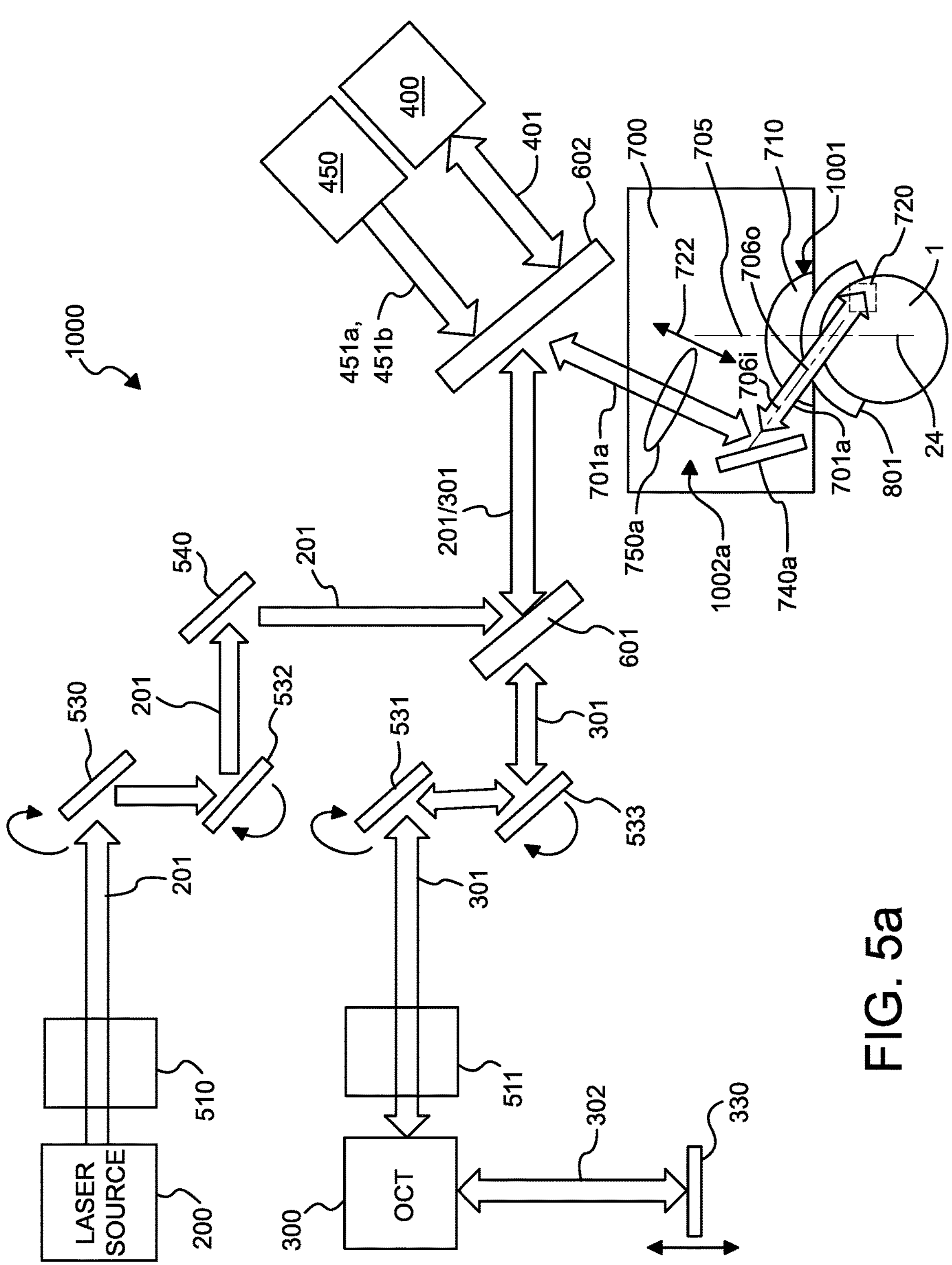
FIG. 5*a* is a detailed block diagram of an integrated surgical system of FIG. 4 configured to deliver one or more light beams along a single beam path to a select tissue target of the eye.

Referring to FIG. 5*a*, in accordance with embodiments disclosed herein an integrated surgical system may include a single optical transmission subsystem and an optics assembly configured to deliver one or more of a laser beam 201, an OCT beam 301, a visual observation beam 401, and a pair of aiming beams of light 451*a*, 451*b* in the distal direction toward an eye 1 along a single beam path, and to receive one or more of an OCT return beam 301 and a visual observation reflection beam 401 back from the eye 1 along the single beam path. In the example embodiment of FIG. 5*a*, the single beam path is into a target volume 720 of ocular tissue of the eye in the irido-corneal angle. In accordance with embodiments disclosed above with reference to FIG. 3, the single beam path may be into other target volumes 720 of ocular tissue of the eye including the cornea, the crystalline lens, the posterior capsule of the lens, the anterior capsule of the lens, the vitreous humor, and the retina.

Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, a pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511 and a transversal scanner with scanning mirrors 531 and 533. Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 210/301 are multiplexed and travel in the same direction. The combined laser/OCT beam 210/301 propagates to a second beam combining mirror 602 where it is combined with one or more aiming beams of light 451*a*/451*b* and a visual observation beam 401 to form a combined laser/OCT/visual/aiming beam 701*a*.

The combined light beam 701*a* (hereinafter referred to as a first light beam) traveling in the distal direction passes through a focusing objective 750*a* and is reflected by an alignment mechanism 740*a*, e.g., a beam-folding mirror, into alignment with an input axis 706*i* of an exit lens 710 of an optics assembly 1001. The alignment mechanism 740*a* and the focusing objective 750*a* are components of an optical transmission subsystem 1001*a* that may move the first light beam 701*a* into alignment with any one of a number of input axes 706*i* of the optics assembly 1001. The first light beam 701*a* passes through the exit lens 710 and exits the exit lens along an output axis 706*o* and into and through a window 801 of a patient interface into a focal point in the target volume 720. The focusing objective 750*a*, which may include a single lens or a group of lenses, is movable in the axial direction 722 by a servo motor, stepper motor or other control mechanism. Movement of the focusing objective 750*a* in the axial direction 722 changes the axial distance of the focus of the laser beam 201 and the OCT beam 301 at a focal point.

A scattered OCT return beam 301 from the target volume 720 of ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300.

Multiple Optical Transmission Subsystems

Figure 5B:
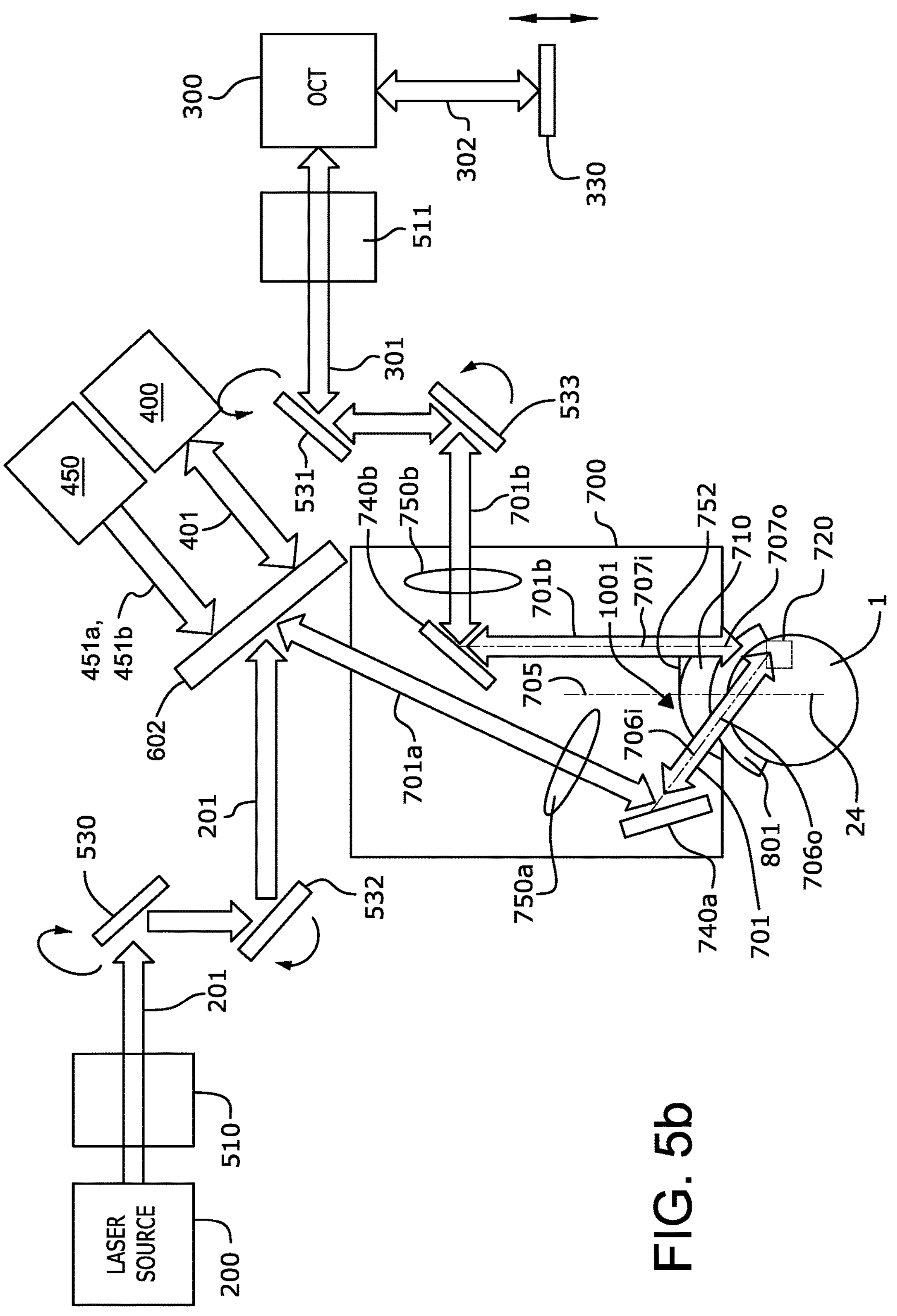
FIG. 5*b* is a detailed block diagram of an integrated surgical system of FIG. 4 configured to deliver one or more light beams along a multiple beam paths to a select tissue target of the eye.

Referring to FIG. 5*b*, in accordance with embodiments disclosed herein an integrated surgical system may include multiple optical transmission subsystems and an optics assembly configured to deliver one or more of a laser beam 201, an OCT beam 301, a visual observation beam 401, and a pair of aiming beams of light 451*a*, 451*b* in the distal direction toward an eye 1, along either of multiple beam paths and to receive one or more of an OCT return beam 301 and a visual observation reflection beam 401 back from the eye 1 along either of multiple beam paths. In the example embodiment of FIG. 5*b*, the laser beam 201 and the visual observation beam 401 are delivered along a first optical path or first beam path into a region of the eye 1 that includes a target volume 720, while the OCT beam 301 is delivered along a second optical path or second beam path into the same region of the eye. The laser beam 201 and the OCT beam 301 are thus co-targeted, non-colinear beams. As shown in FIG. 5*b*, the first beam path and the second beam path are into a target volume 720 of ocular tissue of the eye in the irido-corneal angle. In accordance with embodiments disclosed above with reference to FIG. 3, the laser beam 201 and the OCT beam 301 may be co-targeted along different beam paths into other target volumes 720 of ocular tissue of the eye including the cornea, the crystalline lens, the posterior capsule of the lens, the anterior capsule of the lens, the vitreous humor, and the retina. Alternatively, the laser beam 201 and the OCT beam 301 may be targeted along different beam paths into different target volumes 720.

Regarding the delivery of a laser beam, a laser beam 201 output by the femtosecond laser source 200 passes through a beam conditioner 510 where the basic beam parameters, beam size, divergence are set. The beam conditioner 510 may also perform additional functions, such as setting the beam power or pulse energy and shuttering the beam to turn it on or off. After existing the beam conditioner 510, the laser beam 210 enters a pair of transverse scanning mirrors 530, 532 rotated by a galvanometer scanner scan the laser beam 201 in two essentially orthogonal transversal directions, e.g., in the x and y directions. Then the laser beam 201 is directed towards a beam combining mirror 602 configured to combine the laser beam 201 with a visual observation beam 401 and dual aiming beams 451*a*/451*b* to form a combined laser/OCT/visual/aiming beam 701*a*.

The combined light beam 701*a* (hereinafter referred to as a first light beam) traveling in the distal direction passes through a first focusing objective 750*a* and is directed by a first alignment mechanism 740*a*, e.g., a beam-folding mirror, into alignment with a first input axis 706*i* of an exit lens

710 of an optics assembly 1001. The first alignment mechanism 740*a* and the first focusing objective 750*a* are components of a first optical transmission subsystem 1002*a* that may move the first light beam 701*a* into alignment with any one of a number of first input axes 706*i* of the optics assembly 1001. The first light beam 701*a* passes through the exit lens 710 and exits the exit lens along a first output axis 706*o* and into and through a window 801 of a patient interface into a focal point in the target volume 720. The first focusing objective 750*a*, which may include a single lens or a group of lenses, is movable in the axial direction 722 by a servo motor, stepper motor or other control mechanism. Movement of the first focusing objective 750*a* in the axial direction 722 changes the axial distance of the focus of the laser beam 201 component of the first light beam 701*a* at a focal point.

Regarding delivery of an OCT beam, an OCT beam 301 output by the OCT imaging apparatus 300 passes through a beam conditioner 511 and a transversal scanner with scanning mirrors 531, 533. Proceeding in the distal direction toward the eye 1, after the scanning mirrors 531 and 533, the OCT beam 301 (hereinafter referred to as a second light beam) passes through a second focusing objective 750*b* and is directed by a second alignment mechanism 740*b*, e.g., a beam-folding mirror, into alignment with a second input axis 707*i* of a prism 752 of the optics assembly 1001. The second alignment mechanism 740*b* and the second focusing objective 750*b* are components of a second optical transmission subsystem 1002*b* that may move the second light beam 701*b* into alignment with any one of a number of second input axes 707*i* of the optics assembly 1001. The second light beam 701*b* then passes through the prism 752 and the exit lens 710 of the optics assembly 1001 and exits the exit lens along a second output axis 707*o* and into and through the window 801 of the patient interface into a focal point in the target volume 720. The second focusing objective 750*b*, which may include a single lens or a group of lenses, is movable in the axial direction 723 by a servo motor, stepper motor or other control mechanism. Movement of the second focusing objective 750*b* in the axial direction 723 changes the axial distance of the focus of the OCT beam 301 at a focal point.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300.

Symmetric Optics Assemblies

Figure 6A:
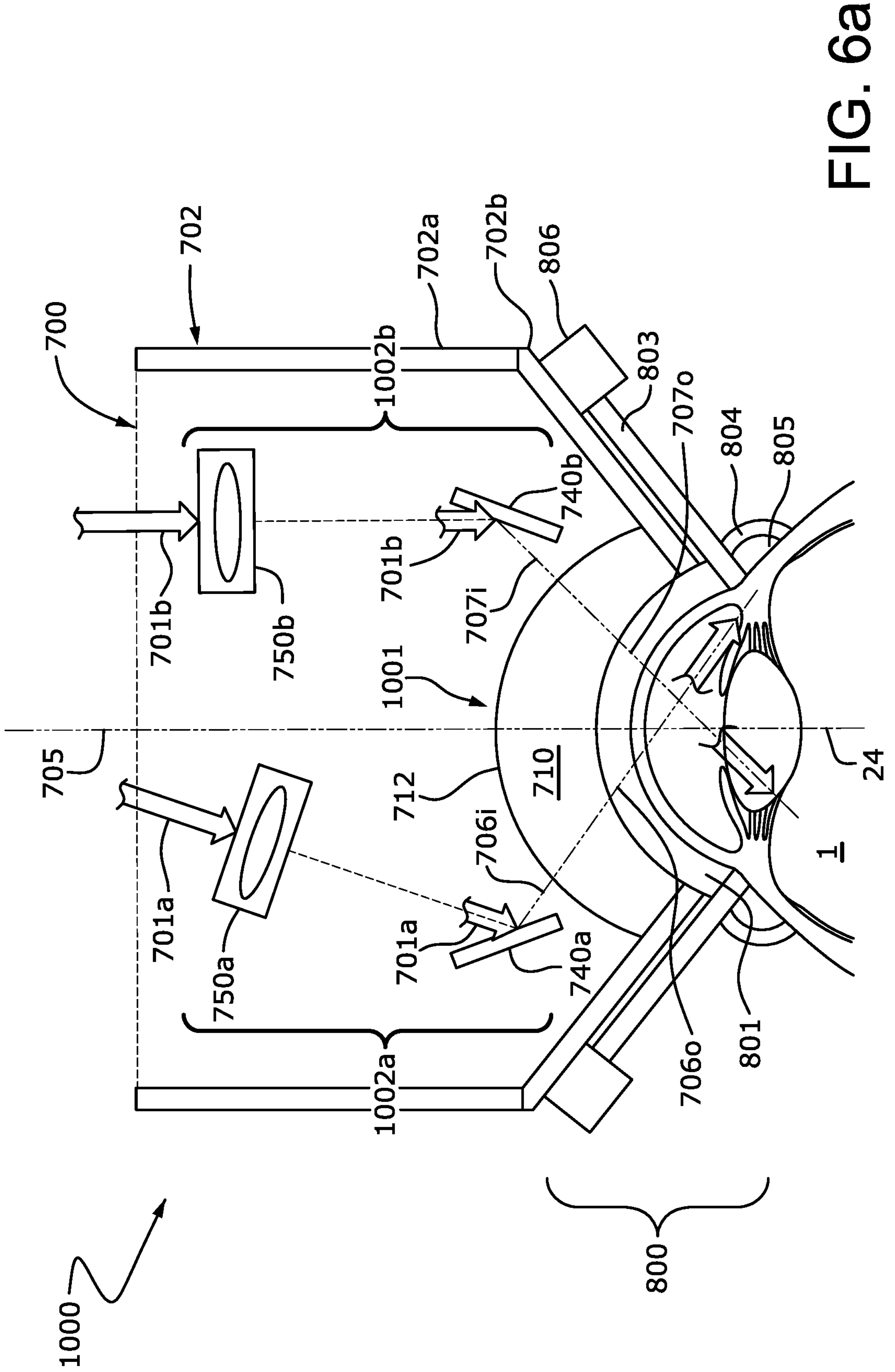
FIGS. 6*a* and 6*b* are schematic illustrations of an embodiment of an integrated surgical system having a focusing objective head with a symmetric optics assembly coupled to an eye through a patient interface.
Figure 6B:
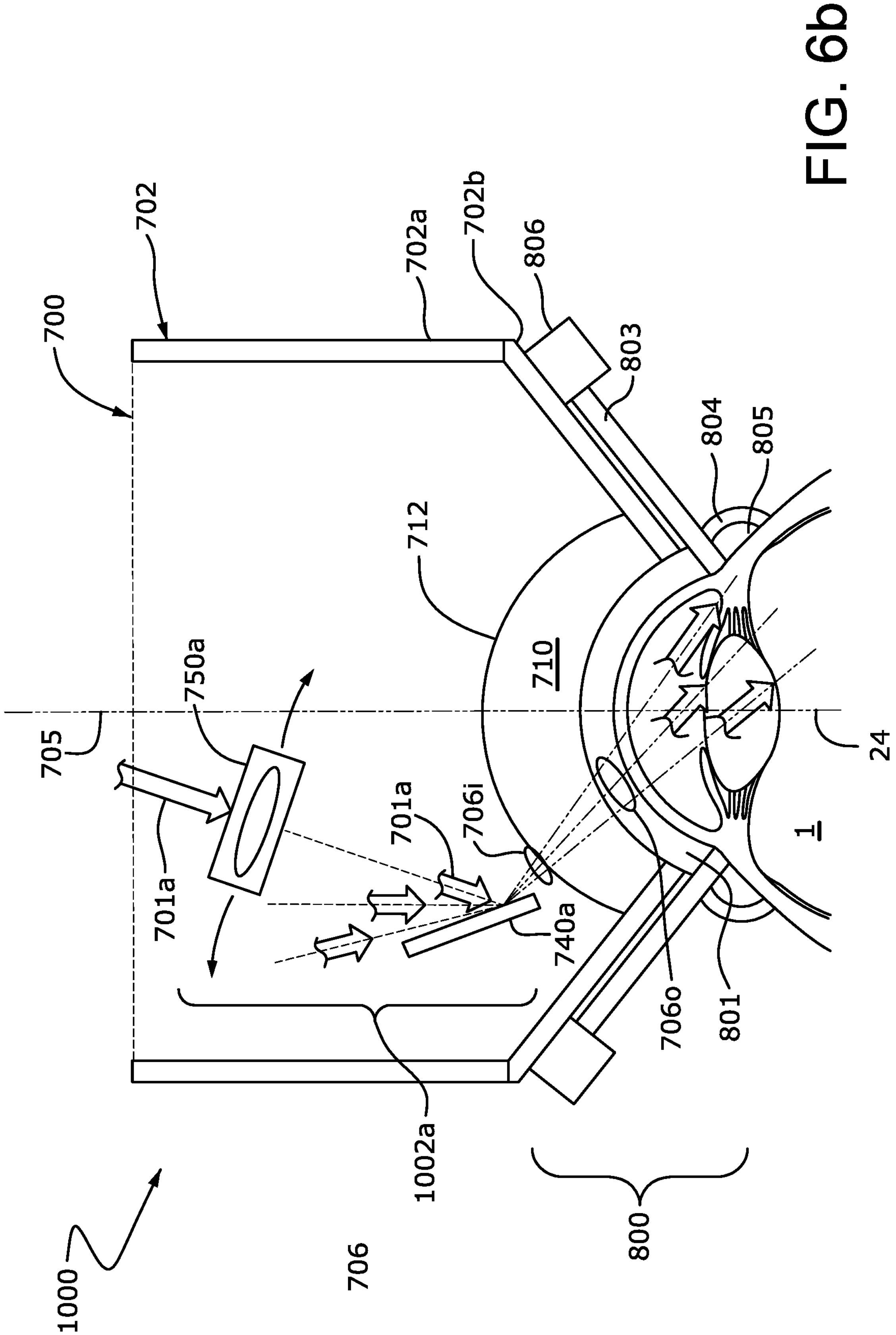

FIGS. 6*a* and 6*b* are schematic illustrations of an embodiment of a focusing objective head 700 of an integrated surgical system 1000 having a symmetric optics assembly 1001 optically coupled with a first optical transmission subsystem 1002*a* and an optional second optical transmission subsystem 1002*b*, each of which are optically coupled with respective components (not shown) to receive a first light beam 701*a* and a second light beam 701*b*. The optics assembly 1001 is mechanically coupled to a non-rotatable distal portion 702*b* of a housing 702 of the focusing objective head 700 while one or more components of the first optical transmission subsystem 1002*a* and the optional second optical transmission subsystem 1002*b* are mechanically coupled to a rotatable proximal portion 702*a* of the housing. Thus, in this embodiment the first optical transmission subsystem 1002*a* and the second optical transmission subsystem 1002*b* (if present) may be rotated relative to the optics assembly 1001, which remains fixed in place relative to the eye. While details of the mechanical coupling of the optics assembly 1001, the first optical transmission subsystem 1002*a* and the second optical transmission subsystem 1002*b* to the housing 702 are not illustrated, various means or mechanisms may be used to secure these components to the interior of the housing at appropriate locations to maintain their respective optical couplings.

Continuing with the embodiment of FIGS. 6*a* and 6*b*, the optics assembly 1001 includes an exit lens 710. The first optical transmission subsystem 1002*a* includes a first focusing objective 750*a* and a first alignment mechanism 740*a* and is optically coupled to receive the first light beam 701*a* incident a surface 712 of the exit lens 710 along a first input axis $\mathbf{706}_i$. The surface 712 of the exit lens 710 to which the first light beam 701*a* is incident may be referred to herein an incident surface of the optics assembly 1001 or an entry surface of the optics assembly. The exit lens 710 directs the first light beam 701*a* into alignment with a first output axis 7060 of the optics assembly 1001. The first light beam 701*a* may be a laser beam, an OCT beam, a visual observation beam, dual aiming beams, or any other type of light beam or a combination thereof. The optional second optical transmission subsystem 1002*b* includes a second focusing objective 750*b* and a second alignment mechanism 740*b* and is optically coupled to receive a second light beam 701*b* incident a surface of the exit lens 710 along a second input axis $\mathbf{707}_i$. The exit lens 710 directs the second light beam 701*b* into alignment with a second output axis 7070 of the optics assembly 1001. The second light beam 701*b* may be a laser beam, an OCT beam, a visual observation beam, dual aiming beams, or any other type of light beam or a combination thereof.

The optics assembly 1001 has an optical axis 705. The optics assembly 1001 is configured to couple to the eye through a patient interface 800 to align its optical axis 705 with the optical axis 24 of the eye. The optics assembly 1001 is optically coupled with the first optical transmission subsystem 1002*a* to receive the first light beam 701*a* along one of a plurality of first input axes $\mathbf{706}_i$ incident an incident surface 712 of the optics assembly and to direct the light beam through the optics assembly to a corresponding one of a plurality of first output axes 7060 aligned with a corresponding one of the plurality of target volumes of ocular tissue in the eye.

With reference to FIG. 6*b* (wherein for clarity of illustration, the optional second optical transmission subsystem 1002*b* is not shown), in some configurations the first alignment mechanism 740*a* of the first optical transmission subsystem 1002*a* comprises a means to direct the first light beam 701*a* into alignment with a select one of first input axes $\mathbf{706}_i$ of the optics assembly 1001. To this end, the first alignment mechanism 740*a* is positioned and oriented relative to the incident surface 712 of the optics assembly 1001 and is configured to be repositioned and/or reoriented relative to the incident surface to direct the first light beam 701*a* into alignment with the selected first input axis $\mathbf{706}_i$ of the optics assembly.

In some embodiments the first alignment mechanism 740*a* may comprise an adjustable reflecting surface optically aligned to receive the first light beam 701*a* along an angle of incidence and to reflect the light beam at an angle of reflection into alignment with the corresponding one of the plurality of first input axes $\mathbf{706}_i$ of the optics assembly 1001. The reflecting surface may be for example, an actuated flip mirror or an actuated angular deflector that is repositioned and/or reoriented through a control signal from a control system 100. Alternatively, simultaneous reorientation of the pair of transverse scanning mirrors 530, 532 and repositioning of the focusing objective 750*a* facilitates aligning the first light beam 701*a* with selected first input axes 706$_i$. The combination of movements of pair of transverse scanning mirrors 530, 532 and the first alignment mechanism 740*a* allows controlling both the location and the angle of the first input axes 706$_i$. When the aperture of the objective of the first optical transmission subsystem 1002*a* is designed to be oversized to accept an extended range of field positions of input and output light beams, repositioning of the focusing objective 750*a* may not be necessary.

In some embodiments the first alignment mechanism 740*a* may comprise a fiber-optic cable and a positioning mechanism. The fiber-optic cable is configured to transmit light and has a light-input end coupled to receive the first light beam 701*a* and a light-output end configured to output the first light beam. The positioning mechanism is mechanically coupled to the fiber-optic cable and is configured to reposition and/or reorient the light-output end into alignment with the selected first input axis 706$_i$ of the optics assembly in response to a control signal from a control system 100.

With continued reference to FIG. 6*b*, in other configurations the first focusing objective 750*a* of the first optical transmission subsystem 1002*a* may be configured to move relative to the first alignment mechanism 740*a* to direct the first light beam 701*a* into alignment with a select one of first input axes 706$_i$ of the optics assembly 1001. To this end, the first focusing objective 750*a* is positioned and oriented relative to the first alignment mechanism 740*a* and is configured to be mechanically repositioned and/or reoriented relative to the first alignment mechanism to direct the first light beam 701*a* into the first alignment mechanism at an angle of incidence that aligns the first light beam with the selected first input axis 706$_i$ of the optics assembly. For example, the first focusing objective 750*a* may be mounted for rotational movement relative to a reflecting surface of the first alignment mechanism 740*a*. A control signal from the control system 100 controls the position and orientation of the first focusing objective 750*a*.

In other configurations, both of the first alignment mechanism 740*a* and the first focusing objective 750*a* may be configured to move to direct the first light beam 701*a* into alignment with a select one of first input axes 706$_i$ of the optics assembly 1001. In the foregoing example embodiments of FIG. 6*b*, three different first input axes 706$_i$ of the optics assembly 1001 are illustrated. It is understood, however, that the number of first input axes 706$_i$ is not limited to three and may essentially comprise an almost infinite number of axes.

With reference to FIG. 6*a*, the optics assembly 1001 is optically coupled with the second optical transmission subsystem 1002*b* (if present) to receive the second light beam 701*b* along one of a plurality of second input axes 707$_i$ incident the incident surface 712 of the optics assembly and to direct the second light beam to a corresponding one of a plurality of second output axes 7070 aligned with a corresponding one of the plurality of target volumes of ocular tissue in the eye. The second optical transmission subsystem 1002*b* may be configured the same as the first optical transmission subsystem 1002*a* as described above. In other words, the second alignment mechanism 740*b* may be positioned and oriented relative to the incident surface 712 of the optics assembly 1001 and configured to be repositioned and/or reoriented relative to the incident surface to direct the second light beam 701*b* into alignment with the selected second input axis 707$_i$ of the optics assembly. Likewise, the second focusing objective 750*b* may be positioned and oriented relative to the second alignment mechanism 740*b* and configured to be mechanically repositioned and/or reoriented relative to the second alignment mechanism to direct the second light beam 701*b* into the second alignment mechanism at an angle of incidence that aligns the second light beam with the selected second input axis 707$_i$ of the optics assembly 1001.

In the embodiment of FIGS. 6*a* and 6*b*, components of the first optical transmission subsystem 1002*a* and the second optical transmission subsystem 1002*b* (if present) are configured to rotate about the optical axis 705 of the optics assembly 1001 to align with tissue targets of the eye at different locations around the circumferential angle of the eye, while the optics assembly itself does not rotate and thus remains fixed in place relative to the eye. To this end, as previously disclosed, the optics assembly 1001 is coupled to a non-rotatable distal portion 702*b* of the housing 702 of the focusing objective head 700, while one or more components of the first optical transmission subsystem 1002*a*, e.g., the first alignment mechanism 740*a* and/or the first focusing objective 750*a*, are mechanically coupled to a rotatable proximal portion 702*a* of the housing and arranged relative to other components (e.g., beam conditioners and scanners 500 and beam combiners 600) to maintain optical coupling with these components to receive the first light beam 701*a* regardless of the rotational position of the proximal portion of the housing. Similarly, if a second optical transmission subsystem 1002*b* is present, one or more components of the second optical transmission subsystem 1002*b*, e.g., the second alignment mechanism 740*b* and the second focusing objective 750*b*, may be mechanically coupled to the rotatable proximal portion 702*a* of the housing 702 and arranged relative to other components (e.g., beam conditioners and scanners 500 and beam combiners 600) to maintain optical coupling with these components to receive the second light beam 701*b* regardless of the rotational position of the proximal portion of the housing.

The optics assembly 1001 provides an interface to the eye through a patient interface 800. To this end, the exit lens 710 of the optics assembly 1001 has an eye-facing, concave surface, and a convex surface opposite the concave surface. The convex surface of the exit lens 710 corresponds to the incident surface or entry surface of the optic assembly 1001. The concave surface is configured to couple to a convex surface of a window 801 of the patient interface 800. In some embodiments, like shown in FIGS. 6*a* and 6*b*, the exit lens 710 is aspheric and has a meniscus form. In other configurations the exit lens may be a spherical lens. In one embodiment, the exit lens 710 is formed of fused silica and has a refractive index $n_x$ of 1.45.

The patient interface 800 optically and physically couples the eye 1 to the exit lens 710. The patient interface 800 immobilizes the eye relative to components of the integrated surgical system, creates a sterile barrier between the components and the patient, and provides optical access between the eye and the instrument. The patient interface 800 is a sterile, single use disposable device and it is coupled detachably to the eye 1 and to the exit lens 710. The patient interface 800 includes a window 801 having an eye-facing, concave surface and an objective-facing, convex surface opposite the concave surface. The window 801 thus has a meniscus form. The concave surface is configured to couple to the eye, either through a direct contact or through index matching material, liquid or gel, placed in between the concave surface and the eye 1. The window 801 may be formed of glass and has a refractive index $n_w$. In one embodiment, the window 801 is formed of fused silica and has a refractive index $n_w$ of 1.45.

The window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 6*a* and 6*b*), vacuum forces between the eye and the suction ring attach the eye to the patient interface 800 during surgery. Removing the vacuum releases or detach the eye 1. The end of the patient interface 800 opposite the eye 1 includes an attachment interface 806 configured to attach to the non-rotatable distal portion 702*b* of the housing 702 of the focusing objective head 700 to thereby affix the position of the eye relative to the other components of the integrated surgical system 1000. The attachment interface 806 can work with mechanical, vacuum, magnetic or other principles and it is also detachable from the integrated surgical system.

Asymmetric Optics Assemblies

Figure 7A:
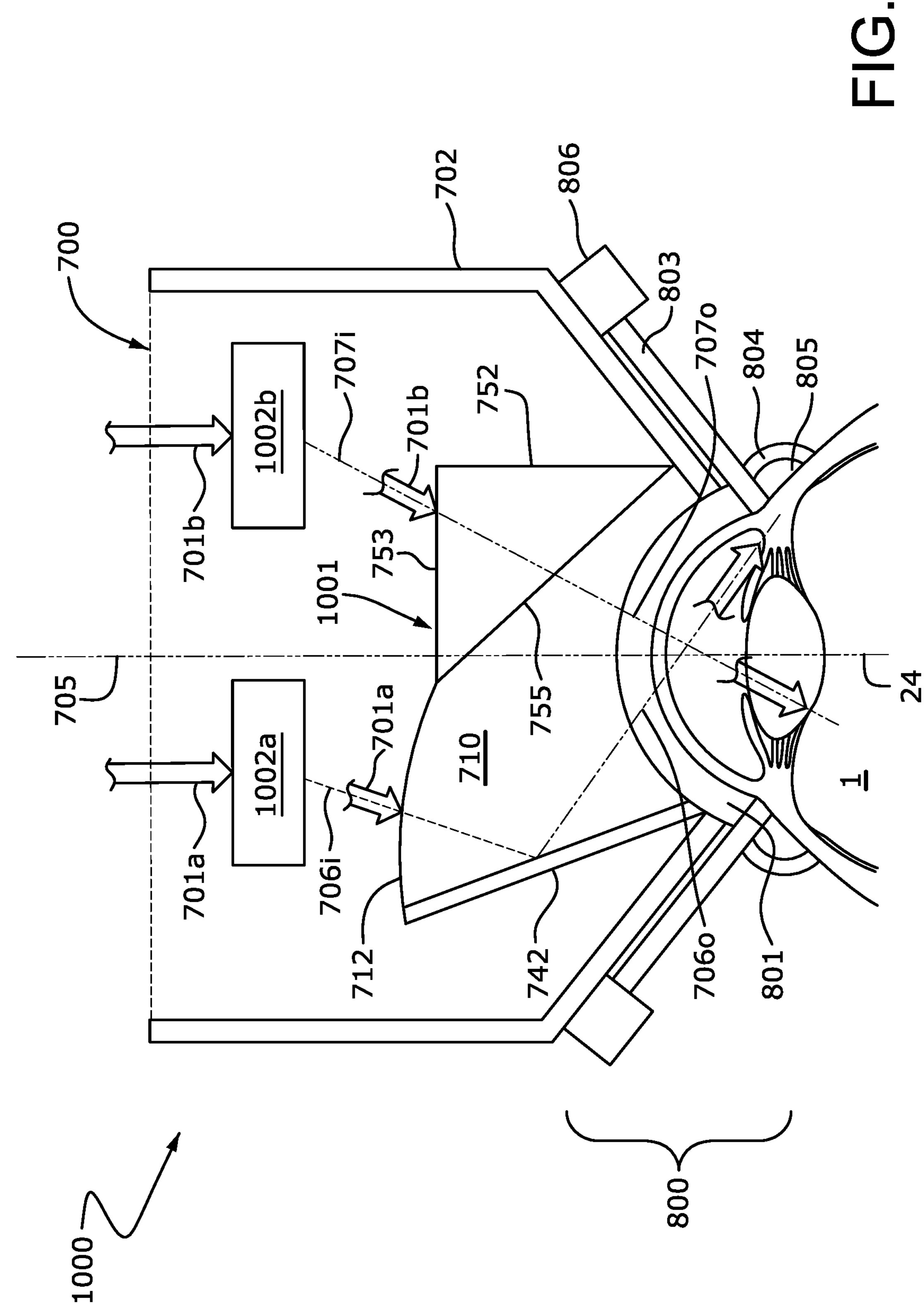
Figure 7B:
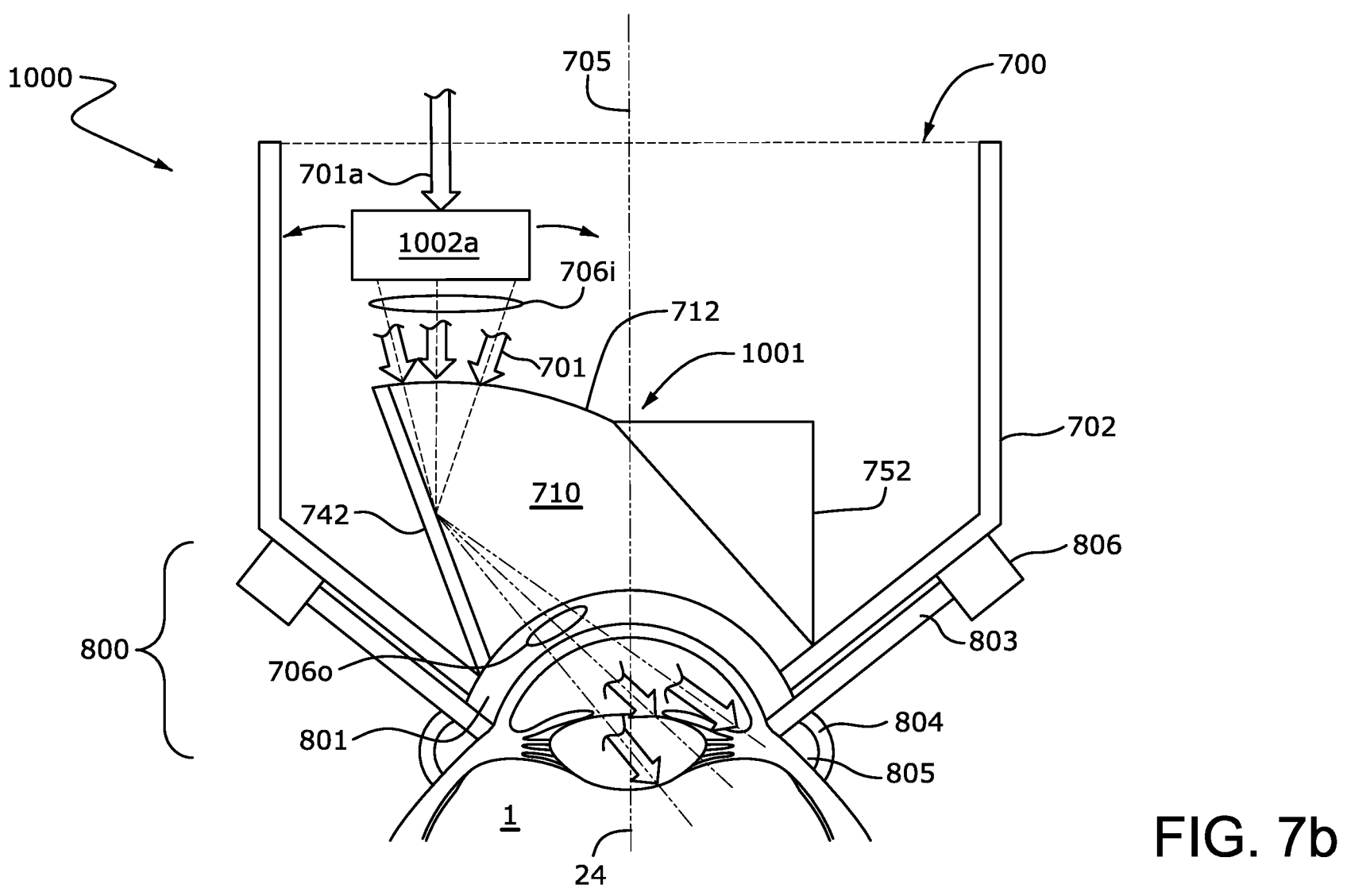

FIGS. 7*a* and 7*b* are schematic illustrations of an embodiment of a focusing objective head 700 of an integrated surgical system 1000 having an asymmetric optics assembly 1001 optically coupled with a first optical transmission subsystem 1002*a* and an optional second optical transmission subsystem 1002*b*, each of which are optically coupled with respective components (not shown) to respectively receive a first light beam 701*a* and a second light beam 701*b*. The optics assembly 1001 is mechanically coupled to a housing 702 of the focusing objective head 700. One or more components of the first optical transmission subsystem 1002*a* and the optional second optical transmission subsystem 1002*b* are also mechanically coupled to the housing 702. Thus, in this embodiment the optics assembly 1001, the first optical transmission subsystem 1002*a* and the second optical transmission subsystem 1002*b* (if present) may be rotated relative to the eye. While details of the mechanical coupling of the optics assembly 1001, the first optical transmission subsystem 1002*a*, and the second optical transmission subsystem 1002*b* to the housing 702 are not illustrated, various means or mechanisms may be used to secure these components to the interior of the housing at appropriate locations to maintain their respective optical couplings.

Continuing with the embodiment of FIGS. 7*a* and 7*b*, the optics assembly 1001 includes a prism 752 and an exit lens 710 having a reflecting surface 742. The first optical transmission subsystem 1002*a* is optically coupled to receive the first light beam 701*a* and to direct the first light beam incident a surface 712 of the exit lens 710 along a first input axis 706*i*. The surface 712 of the exit lens 710 to which the first light beam 701*a* is incident may be referred to herein a first incident surface of the optics assembly 1001 or a first entry surface of the optics assembly. The reflecting surface 742 of the exit lens 710 receives the first light beam 701*a* and reflects the first light beam into alignment with a first output axis 7060 of the optics assembly 1001. The first light beam 701*a* may be a laser beam, an OCT beam, a visual observation beam, dual aiming beams, or any other type of light beam or a combination thereof.

The optional second optical transmission subsystem 1002*b* is optically coupled to receive a second light beam 701*b* and to direct the second light beam incident an entry face 753 of the prism 752 along a second input axis 707*i*. The entry face 753 of the prism 752 may be referred to herein a second incident surface of the optics assembly 1001 or a second entry surface of the optics assembly. The prism 752 directs the second light beam 701*b* to an exit face 755 of the prism and into the exit lens 710, which in turn directs the second light beam into alignment with a second output axis 707*o* of the optics assembly 1001. The second light beam 701*b* may be a laser beam, an OCT beam, a visual observation beam, dual aiming beams, or any other type of light beam or a combination thereof.

Although not illustrated in FIGS. 7*a* and 7*b*, the first optical transmission subsystem 1002*a* may include either or each of a first focusing objective and a first alignment mechanism, and the second optical transmission subsystem 1002*b* may include either or each of a second focusing objective and a second alignment mechanism as described in the embodiments of FIGS. 6*a* and 6*b*. The first optical transmission subsystem 1002*a* and the second optical transmission subsystem 1002*b* may include other components, such as beam conditions and scanners 500 and beam combiners 600.

The optics assembly 1001 has an optical axis 705. The optics assembly 1001 is configured to couple to the eye through a patient interface 800 to align its optical axis 705 with the optical axis 24 of the eye. The optics assembly 1001 is optically coupled with the first optical transmission subsystem 1002*a* to receive the first light beam 701*a* along one of a plurality of first input axes $\mathbf{706}_i$ incident a first incident surface 712 of the optics assembly and to direct the light beam through the optics assembly to a corresponding one of a plurality of first output axes 7060 aligned with a corresponding one of the plurality of target volumes of ocular tissue in the eye.

With reference to FIG. 7*b* (wherein for clarity of illustration, the optional second optical transmission subsystem 1002*b* is not shown), in some configurations the first optical transmission subsystem 1002*a* comprises a means to direct the first light beam 701*a* into alignment with a select one of first input axes $\mathbf{706}_i$ of the optics assembly 1001. To this end, the first optical transmission subsystem 1002*a* may include a first alignment mechanism like the one described above for the embodiments of FIGS. 6*a* and 6*b*. The first alignment mechanism, e.g., actuated flip mirror, an actuated angular deflector, or fiber-optic cable, may be positioned and oriented relative to the first incident surface of the optics assembly 1001 and configured to be repositioned and/or reoriented relative to the incident surface to direct the first light beam 701*a* into alignment with the selected first input axis $\mathbf{706}_i$ of the optics assembly.

With continued reference to FIG. 7*b*, in other configurations one or more components of the first optical transmission subsystem 1002*a* may be configured to move relative to the optics assembly 1001 to align the first light beam 701*a* with a select one of first input axes $\mathbf{706}_i$ of the optics assembly. To this end, the first optical transmission subsystem 1002*a* may include a first focusing objective like the one described above for the embodiments of FIGS. 6*a* and 6*b*. The first focusing objective may be positioned and oriented relative to the incident surface 712 of the optics assembly and configured to be mechanically repositioned and/or reoriented relative to the incident surface to direct the first light beam 701*a* into the exit lens 710 along the selected first input axis $\mathbf{706}_i$ of the optics assembly.

In other configurations, the first optical transmission subsystem 1002*a* may include both of a first alignment mechanism and a first focusing objective. In the foregoing example embodiments of FIG. 7*b*, three different first input axes $\mathbf{706}_i$ of the optics assembly 1001 are illustrated. It is understood, however, that the number of first input axes 706$_i$ is not limited to three and may essentially comprise an almost infinite number of axes.

With reference to FIG. 7*a*, the optics assembly 1001 is optically coupled with the second optical transmission subsystem 1002*b* (if present) to receive the second light beam 701*b* along one of a plurality of second input axes 707$_i$ incident the second incident surface 753 of the optics assembly and to direct the second light beam to a corresponding one of a plurality of second output axes 707$_o$ aligned with a corresponding one of the plurality of target volumes of ocular tissue in the eye. The second optical transmission subsystem 1002*b* may be configured the same as the first optical transmission subsystem 1002*a* as described above.

In the embodiment of FIGS. 7*a* and 7*b*, components of the first optical transmission subsystem 1002*a* and the second optical transmission subsystem 1002*b* (if present) are configured to rotate about the optical axis 705 of the optics assembly 1001 together with the optics assembly while the patient interface 800 remains fixed in place. To this end, the optics assembly 1001 is mechanically coupled to a rotatable housing 702 of the focusing objective head 700 together with one or more components of the first optical transmission subsystem 1002*a*. The components of the first optical transmission subsystem 1002*a* are arranged relative to other components (e.g., beam conditioners and scanners 500 and beam combiners 600) to maintain optical coupling with these components to receive the first light beam 701*a* regardless of the rotational position of the rotatable housing 702. Similarly, if a second optical transmission subsystem 1002*b* is present, one or more components of the first optical transmission subsystem may be mechanically coupled to the housing 702 and arranged relative to other components (e.g., beam conditioners and scanners 500 and beam combiners 600) to maintain optical coupling with these components to receive the second light beam 701*b* regardless of the rotational position of the housing 702. Rotating the housing 702 of the focusing objective head 700 as such, the optics assembly 1001, the first light beam 701*a* and the second light beam 701*b* rotate together relative to the fixed window 801 of the patient interface 800 and around the optical axis 705 of the optics assembly. This allows optical access to various tissue targets of the eye around the 360-degree circumference of the eye 1 by each of light beams 701*a*, 701*b*.

The optics assembly 1001 provides an interface to the eye through the patient interface 800. To this end, the exit lens 710 of the optics assembly 1001 has an eye-facing, concave surface, and a generally convex surface 712 opposite the concave surface. The prism 752 includes an input surface or entry face 753 and an output surface or exit face 755. The generally convex surface 712 of the exit lens 710 includes a modified surface 719 configured to couple to the exit face 755 of the prism 752. In one configuration the modified surface 719 is a flat surface having a geometry that matches the geometry of the exit face 755 of the prism 752. The geometry may be, for example, a rectangle. The exit lens 710 may thus be described as having a generally meniscus form with a modified surface 719. The exit lens 710 and the prism 752 may be formed of a solid material the same as or similar to the window 801 of the patient interface 800. In one embodiment, the exit lens 710 is formed of fused silica and has a refractive index $n_x$ of 1.45. The prism 752 may be formed of fused silica and has a refractive index n p that is the same as that of the exit lens 710. The patient interface 800 optically and physically couples the eye 1 to the exit lens 710. The patient interface 800 may be configured the same as described above with reference to FIGS. 6*a* and 6*b*.

With reference to FIGS. 8*a*, 8*b*, 8*c*, 8*d*, and 8*e*, alternative configurations of the optics assembly 1001 are contemplated, each of which may be used in place of the optics assembly of FIGS. 7*a* and 7*b*. In each of FIGS. 8*a*, 8*b*, 8*c*, 8*d*, and 8*e*, the optics assembly 1001 includes an exit lens 710 that has an entry surface 712 and an extended side region with a reflecting surface 742. The entry surface 712 receives the first light beam 701*a* along a first input axis 706*i* incident the entry surface. The reflecting surface 742 receives the first light beam 701*a* and reflects the first light beam into alignment with a first output axis 706*o* of the optics assembly 1001.

Figures 8A, 8B, 8C, 8D:
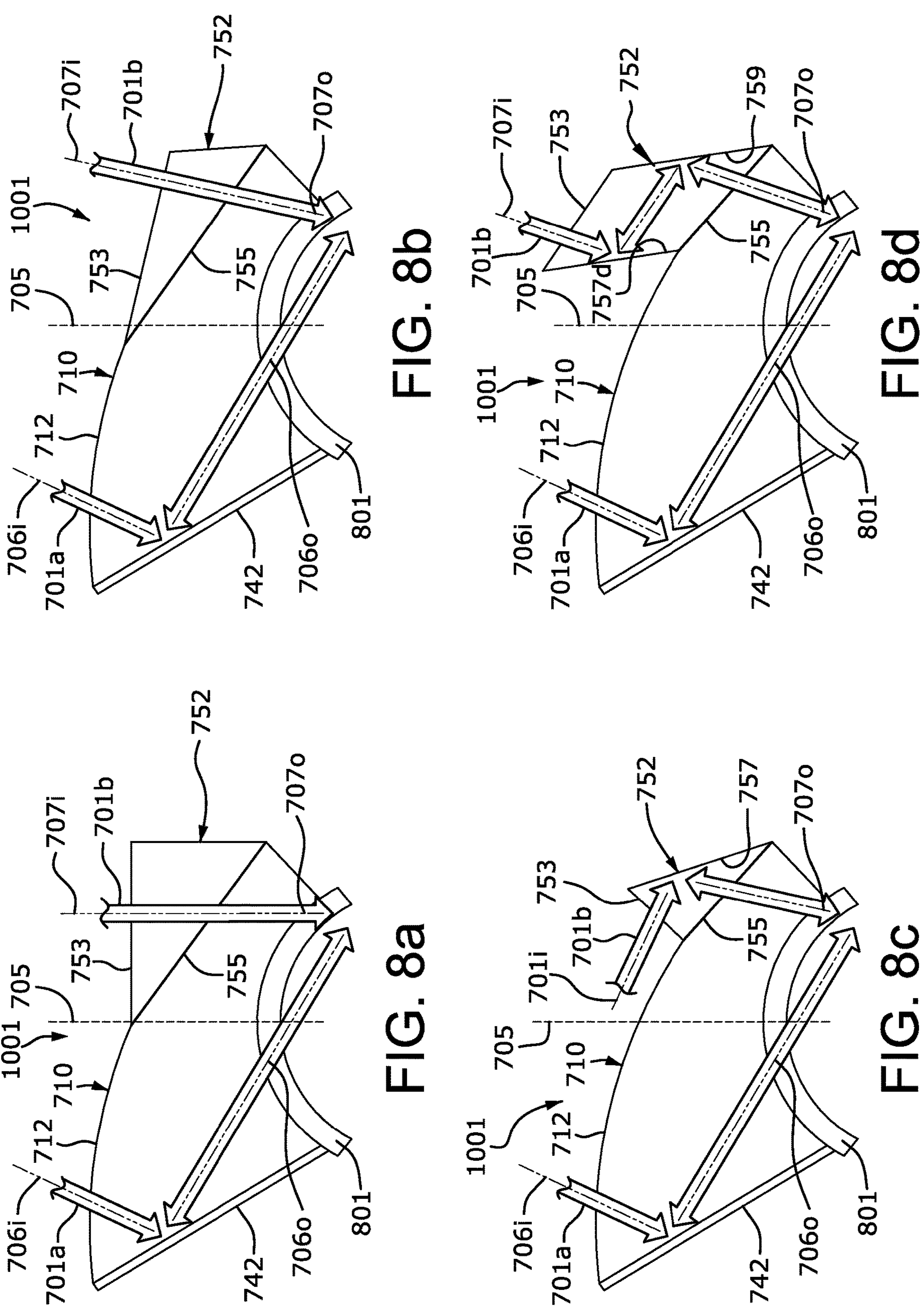
FIGS. 8*a*, 8*b*, 8*c*, and 8*d* are schematic illustrations of other configurations of asymmetric optics assemblies that may be used in place of the optics assembly of FIG. 7*a*.

In FIGS. 8*a* and 8*b*, the prisms 752 are similar to the prism of FIGS. 7*a* and 7*b*. These prisms 752 receive a second light beam 701*b* incident an entry face 753*a*, 753*b* of the prism along a second input axis 707*i* and direct the second light beam 701*b* to an exit face 755 of the prism and into the exit lens 710, which in turn directs the second light beam into alignment with a second output axis 707*o* of the optics assembly 1001.

In FIGS. 8*c*, 8*d* and 8*e*, each of the prisms 752 has one or more reflecting surfaces off which the second light beam 701*b* reflects into an exit lens 710, which in turn directs the second light beam into alignment with a second output axis 707*o* of the optics assembly 1001. In these configurations, the prisms 752 include: 1) an entry face 753, 2) one or more reflective surfaces 757, 759, and 3) an exit face 755. These configurations of prisms 752 are solutions that address two challenges: 1) the very tight space constraints within the focusing objective head 700, and 2) ensuring the second light beam 701*b* reaches the target volume 720.

With reference to the optical assembly of FIG. 8*e*, due to the curved top surface 712*e* of the exit lens 710*e*, without the prism 752*e*, the angle of incidence of the input light beam along the second input axis 707*e*$_i$ would be high and the refraction angle steep. Considering the extremely limited space within the focusing objective head 700, it may be geometrically difficult to direct the second light beam 701*b* at an angle relative to curved top surface 712*e* of the exit lens 710*e* such that the second light beam would strike the target volume 720. To address this, the prism 752 of FIG. 8*e* has three faces: an entry face 753, a reflective surface 757 and an exit face 755. The prism 752 is designed and mechanically positioned so that the nominal second light beam 701*b* angle of incidence on the entry face 753 is normal, and the second light beam scanner (if any) has minor deviation (+/−10 degrees), which minimizes the scanned beams refraction and therefore aberrations. There are several other design measures implemented to reduce the refractive angle change. Firstly, the prism 752 is made from the same material as the exit lens 710. Secondly, a region of the top surface 712 is modified to have an angled flat face machined for prism placement and registration to bond the prism to the exit lens 710. The modified surface 719 includes an angled flat face that is parallel to the exit face 755 of the prism 752. As the exit face 755 of the prism 752 and modified surface 719 are parallel and the prism and exit lens 710 are of the same material, there is no refraction when the second light beam 701*b* traverses the prism-lens interface.

Figure 9:
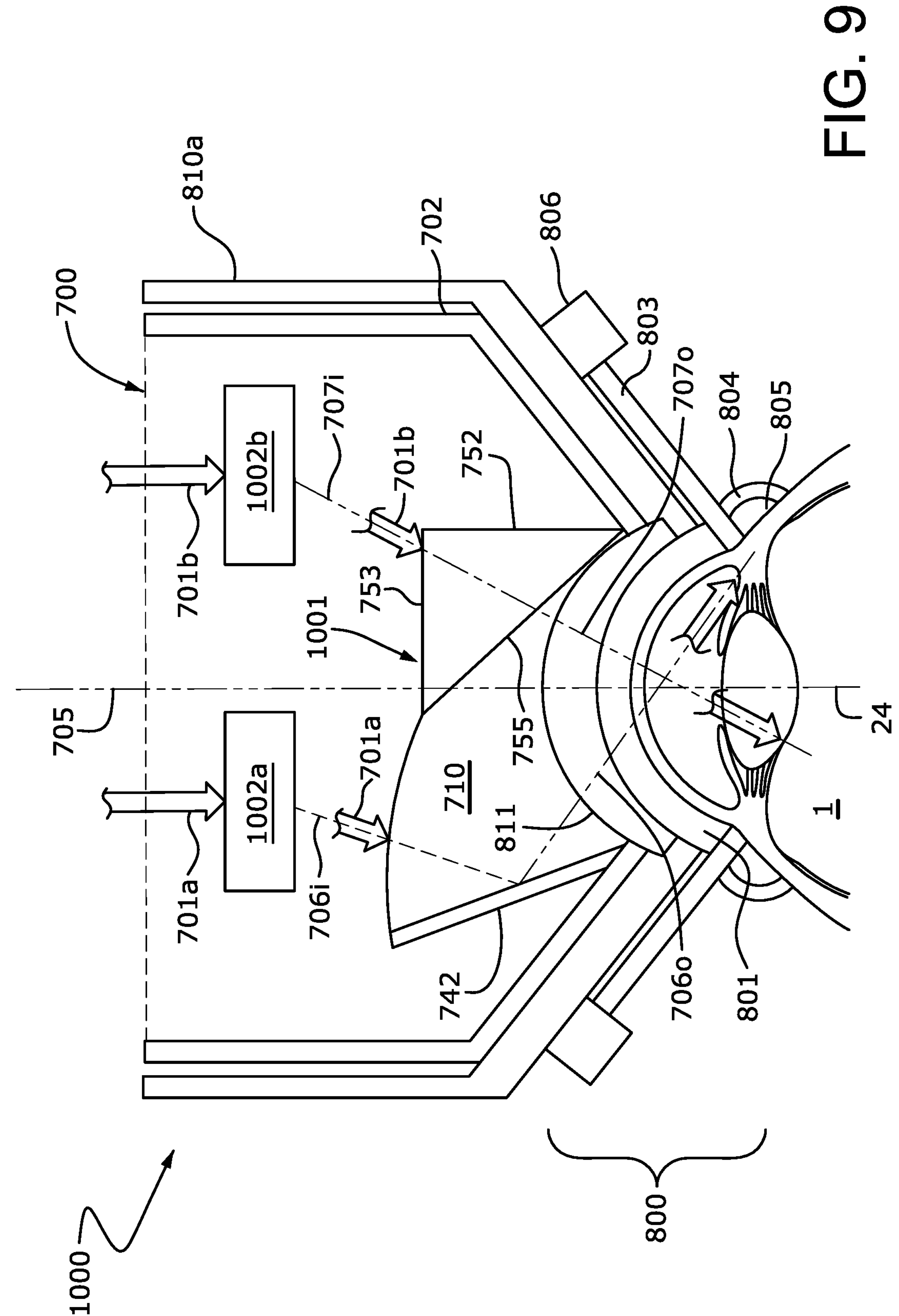
FIG. 9 is a schematic illustration of an embodiment of an integrated surgical system having a focusing objective head rotatably coupled to an eye through an interface structure and a patient interface.
Figure 10:
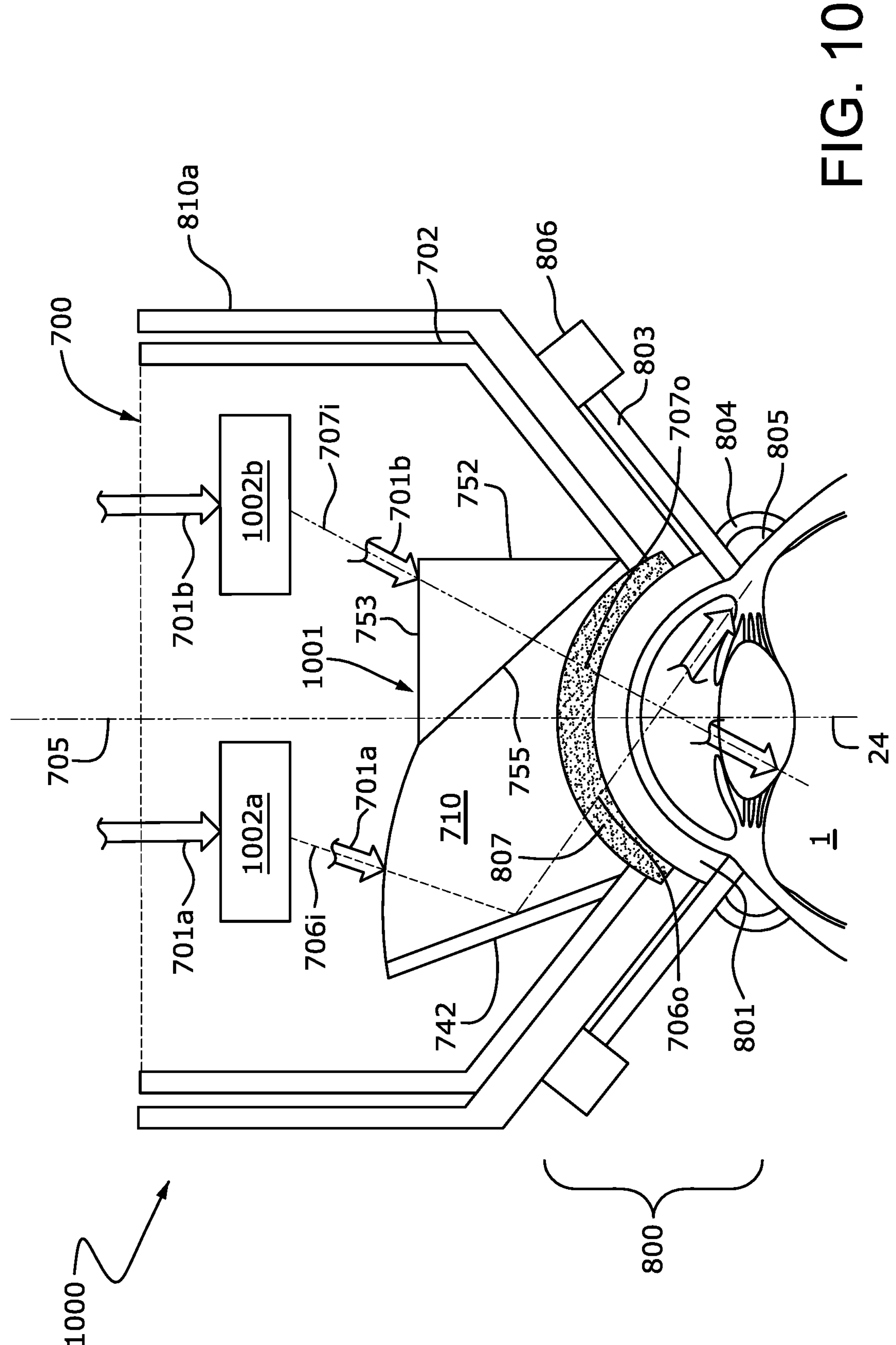
FIG. 10 is a schematic illustration of another embodiment of an integrated surgical system having a focusing objective head rotatably coupled to an eye through an interface structure and a patient interface.

With reference to FIGS. 7*a* and 7*b*, the focusing objective head 700 and the patient interface 800 may be configured such that focusing objective head 700 is able to rotate within the additional component without any rotational torque being transferred to the patient interface 800 that is secured to the eye. To this end, an additional component may be included between the focusing objective head 700 and the patient interface 800. The additional component is fixed in place relative to the patient interface 800 but not the focusing objective head 700. FIGS. 9 and 10 are examples of such configurations.

FIG. 9 is a schematic illustration of a configuration where a housing 702 of a focusing objective head 700 is docked together with a patient interface 800 through an interface structure 810*a* that couples to the patient interface. This docking results in an indirect-contact coupling between the optics assembly 1001 of the focusing objective head 700 and the window 801 of the patient interface 800. The housing 702 of the focusing objective head 700 and the interface structure 810*a* are mechanically configured and coupled together to enable rotation of the optics assembly 1001 and the optical transmission subsystems 1002*a*, 1002*b* within the interface structure, relative to the patient interface 800, which is configured to fixedly couple to the eye and decouple therefrom. In this configuration, the optical transmission subsystems 1002*a*, 1002*b* can rotate about the optical axis 705 of the optics assembly 1001 without any rotational torque being transferred to the patient interface 800 that is secured to the eye. The attachment interface 806 of the patient interface 800 attaches to the non-rotating interface structure 810*a*. Thus, rotation of the focusing objective head 700 does not translate rotational toque to the patient interface coupled to the eye. In this configuration, the interface structure 810*a* includes a transparent window 811 through which light beams 701*a*, 701*b* pass into the window 801 of the patient interface 800.

FIG. 10 is a schematic illustration of other configurations where a housing 702 of the focusing objective head 700 is docked together with a patient interface 800 through an interface structure 810*b* that couples to the patient interface. This docking results in an indirect-contact coupling between the optics assembly 1001 of the focusing objective head 700 and the window 801 of the patient interface 800. Like the configuration of FIG. 9, the housing 702 of the focusing objective head 700 and the interface structure 810*b* are mechanically configured and coupled together to enable rotation of the optics assembly 1001 and the optical transmission subsystems 1002*a*, 1002*b* within the interface structure, relative to the patient interface 800, which is configured to fixedly couple to the eye and decouple therefrom. In this configuration, the optical transmission subsystems 1002*a*, 1002*b* can rotate about the optical axis 705 of the optics assembly 1001 without any rotational torque being transferred to the patient interface 800 that is secured to the eye. The attachment interface 806 of the patient interface 800 attaches to the non-rotating interface structure 810*a*. Thus, rotation of the focusing objective head 700 does not translate rotational toque to the patient interface coupled to the eye. In this configuration, the interface structure 810*b* includes an opening 814 through which through which light beams 701*a*, 701*b* pass into the window 801 of the patient interface 800. An index matching material, liquid, or gel 807 is placed on the convex surface of the window 801 to create a layer between the exit lens 710 and the window upon coupling of the components 800, 810*b*, 700.

Focusing Objective Head

With reference to FIGS. 5*a* through 10, disclosed is a focusing objective head 700 configured to couple to a patient interface 800. The patient interface has a window 801 configured to couple to a cornea 3 of an eye 1 having an optical axis 24. The focusing objective head 700 includes a first optical transmission subsystem 1002*a* that is optically coupled to receive a first light beam 701*a* and an optics assembly 1001 having an optical axis 705. The optics assembly 1001 is configured to couple to the eye such that its optical axis 705 is aligned with the optical axis 24 of the eye. The optics assembly 1001 is optically coupled with the first optical transmission subsystem 1002*a* to receive the first light beam 701*a* along one of a plurality of first input axes 706*i* and to direct the first light beam to a corresponding one of a plurality of first output axes 706*o* aligned with a corresponding one of a plurality of target volumes 720 of ocular tissue in the eye.

The first optical transmission subsystem 1002*a* is configured to direct the first light beam 701*a* into alignment with a select one of the plurality of first input axes 706*i*. To this end, the first optical transmission subsystem includes a means 740*a* for aligning the first light beam 701*a* with the one of the plurality of first input axes 706*i*. In some embodiments, the means for aligning the first light beam 701*a* with the one of a plurality of first input axes 706*i* includes at least one adjustable reflecting surface 740*a* optically aligned to receive the first light beam along an angle of incidence and to reflect the first light beam at an angle of reflection into alignment with the corresponding one of the plurality of first input axes.

In some embodiments, the first optical transmission subsystem 1002*a* is optically coupled to receive a plurality of different types of light beams and includes a means for colinearly combining 600 the plurality of light beams into the first light beam 701*a*. In some embodiments, the first optical transmission subsystem 1002*a* includes a focusing objective 750*a* configured to be controlled by a control system 100 to focus the first light beam 701*a* at the corresponding one of the plurality of target volumes 720 of ocular tissue.

The focusing objective head 700 includes a housing 702 configured to rotate the first optical transmission subsystem 1002*a* about the optical axis 705 of the optics assembly 1001. To this end, one or more components 740*a*, 750*a*, 500, and/or 600 of the first optical transmission subsystem 1002*a* are mechanically coupled to the housing 702 to rotate about the optical axis 705 of the optics assembly 1001. The optics assembly 1001 may also be mechanically coupled to the housing 702 to rotate about the optical axis 705 of the optics assembly.

In some embodiments, the focusing objective head 700 includes a second optical transmission subsystem 1002*b* that is optically coupled to receive a second light beam 701*b*. The optics assembly 1001 is optically coupled with the second optical transmission subsystem 1002*b* to receive the second light beam 701*b* along one of a plurality of second input axes 707*i* and to direct the second light beam to a corresponding one of a plurality of second output axes 707*o* aligned with a corresponding one of the plurality of target volumes 720 of ocular tissue in the eye.

The second optical transmission subsystem 1002*b* is configured to direct the second light beam 701*b* into alignment with a select one of the plurality of second input axes 707*i*. To this end, the second optical transmission subsystem 1002*b* includes a means 740*b* for aligning the second light beam 701*b* with the one of the plurality of second input axes 707*i*. In some embodiments, the means for aligning the second light beam 701*b* with the one of a plurality of second input axes 707*i* includes at least one adjustable reflecting surface 740*b* optically aligned to receive the second light beam along an angle of incidence and to reflect the second light beam at an angle of reflection into alignment with the corresponding one of the plurality of second input axes.

In some embodiments the second optical transmission subsystem 1002*b* is optically coupled to receive a plurality of different types of light beams and includes a means 600 for colinearly combining the plurality of light beams into the second light beam 701*b*. The second optical transmission subsystem 1002*b* includes a focusing objective 750*b* configured to focus the second light beam 701*b* at the corresponding one of the plurality of target volumes 720 of ocular tissue. One or more components 740*b*, 750*b*, 500, and/or 600 of the second optical transmission subsystem 1002*b* are mechanically coupled to the housing 702 configured to rotate the portion of the second optical transmission subsystem about the optical axis 705 of the optics assembly 1001.

Method of Accessing Tissue Targets

Figure 11:
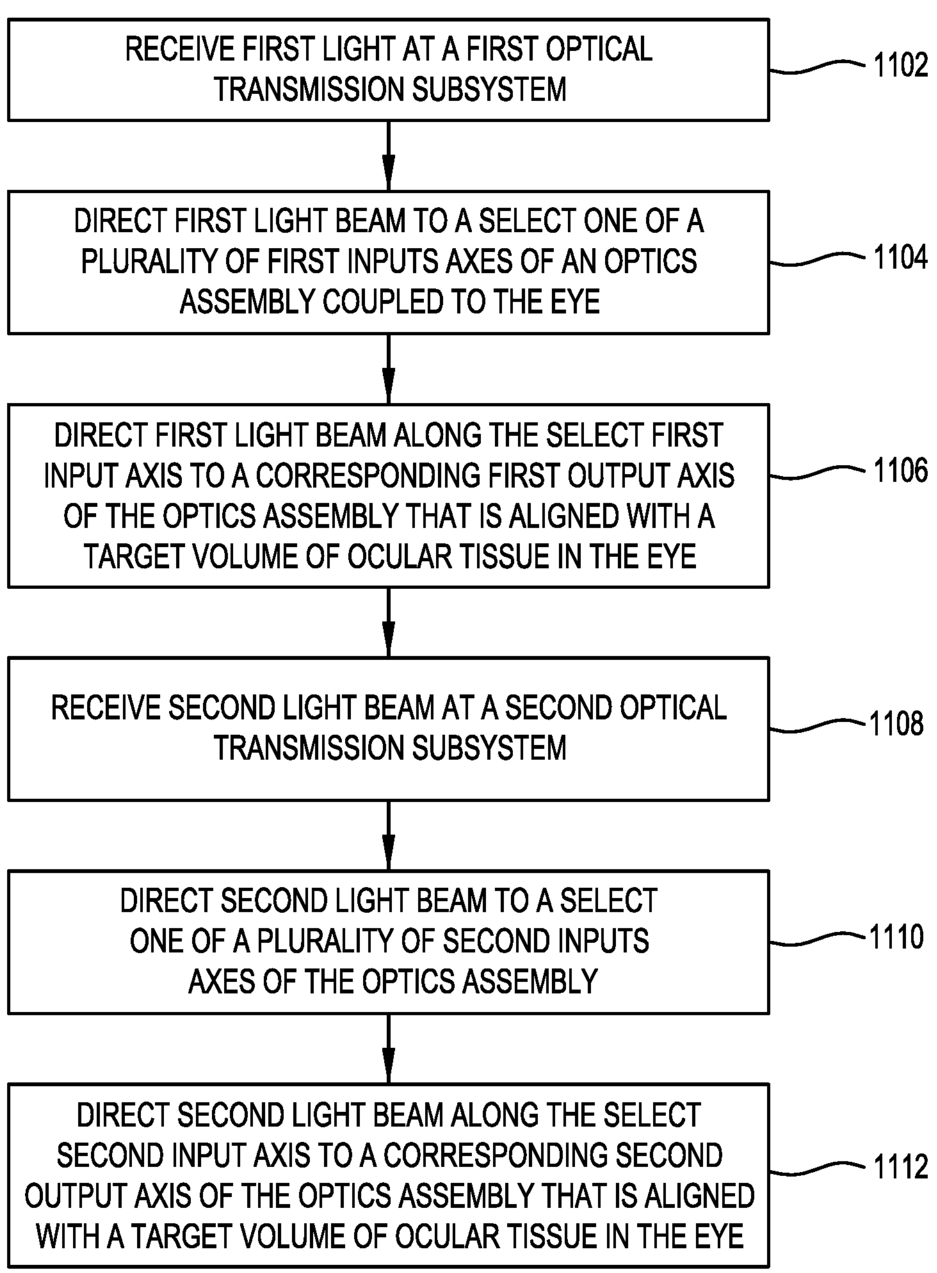
FIG. 11 is a flowchart of a method of accessing one of a plurality of target volumes of ocular tissue in an eye.

With reference to FIG. 11, a method of accessing one of a plurality of target volumes of ocular tissue in an eye is described. The method may be performed using an integrated surgical system configured as describe above with reference to FIGS. 4-10.

At block 1102 and with additional reference to FIG. 4-10, a first light beam 701*a* is received at a first optical transmission subsystem 1002*a*. The first light beam 701*a* may be one of a laser beam, an OCT beam, a visual observation beam, and dual aiming beams. The first light beam may be a colinear combination of two or more of a laser beam, an OCT beam, a visual observation beam, and dual aiming beams.

At block 1104, the first light beam 701*a* is directed by the first optical transmission subsystem 1002*a* to a select one of a plurality of first inputs axes 706*i* of an optics assembly 1001 coupled to the eye. To this end, the position of an alignment mechanism of the first optical transmission subsystem 1002*a* may be controlled, e.g., rotated, flipped, etc., to direct the first light beam 701*a* into alignment with the selected first input axis 706*i.*

At block 1106, the first light beam 701*a* is directed by the optics assembly 1001 along the select one of the plurality of first inputs axes 706*i* to a corresponding one of a plurality of first output axes 706*o* of the optics assembly that is aligned with a corresponding one of the plurality of target volumes 720 of ocular tissue in the eye. Directing the first light beam 701*a* may include reflecting or bending the first light beam through one or more optics of the optics assembly.

At block 1108, a second light beam 701*b* is received at a second optical transmission subsystem 1002*b*. The second light beam 701*b* may be received simultaneously with the first light beam 701*a*. The second light beam 701*b* may be one of a laser beam, an OCT beam, a visual observation beam, and dual aiming beams. The second light beam may be a colinear combination of two or more of a laser beam, an OCT beam, a visual observation beam, and dual aiming beams.

At block 1110, the second light beam 701*b* is directed by the second optical transmission subsystem 1002*b* to a select one of a plurality of second inputs axes 707*i* of the optics assembly 1001. To this end, the position of an alignment mechanism of the second optical transmission subsystem 1002*b* may be controlled, e.g., flipped, rotated, etc., to direct the second light beam 701*b* into alignment with the selected second input axis 707*i.*

At block 1112, the second light beam 701*b* is directed by the optics assembly 1001 along the select one of the plurality of second inputs axes 707*i* to a corresponding one of a plurality of second output axes 707*o* of the optics assembly aligned with a corresponding one of the plurality of target volumes 720 of ocular tissue in the eye. Directing the second light beam 701*b* may include reflecting or bending the second light beam through one or more optics of the optics assembly.

In some methods, the target volume 720 of ocular tissue aligned with the first output axes 706*o* of the optics assembly 1001 and the target volume of ocular tissue aligned with the second output axes 707*o* of the optics assembly may be the same target volume. For example, with reference to FIG. 5*b*, both of the first output axes 706*o* and the second output axes 707*o* of the optics assembly may align with a target volume 720 in the irido-corneal angle of the eye. In other methods, the target volume 720 of ocular tissue aligned with the first output axes 706*o* of the optics assembly 1001 and the target volume of ocular tissue aligned with the second output axes 707*o* of the optics assembly may be different target volumes.

Minimally Invasive Surgical Treatments

Access to select different targets of the eye enables minimally invasive surgical treatment for various conditions. For example, it may be desirable to access one or more of including the irido-corneal angle, the cornea, the crystalline lens, the posterior capsule of the lens, the anterior capsule of the lens, the vitreous humor, and the retina. It may also be desirable to simultaneously access different targets of the eye. Described below is an example treatment for glaucoma through access of the irido-corneal angle.

Glaucoma Treatment

Figure 12:
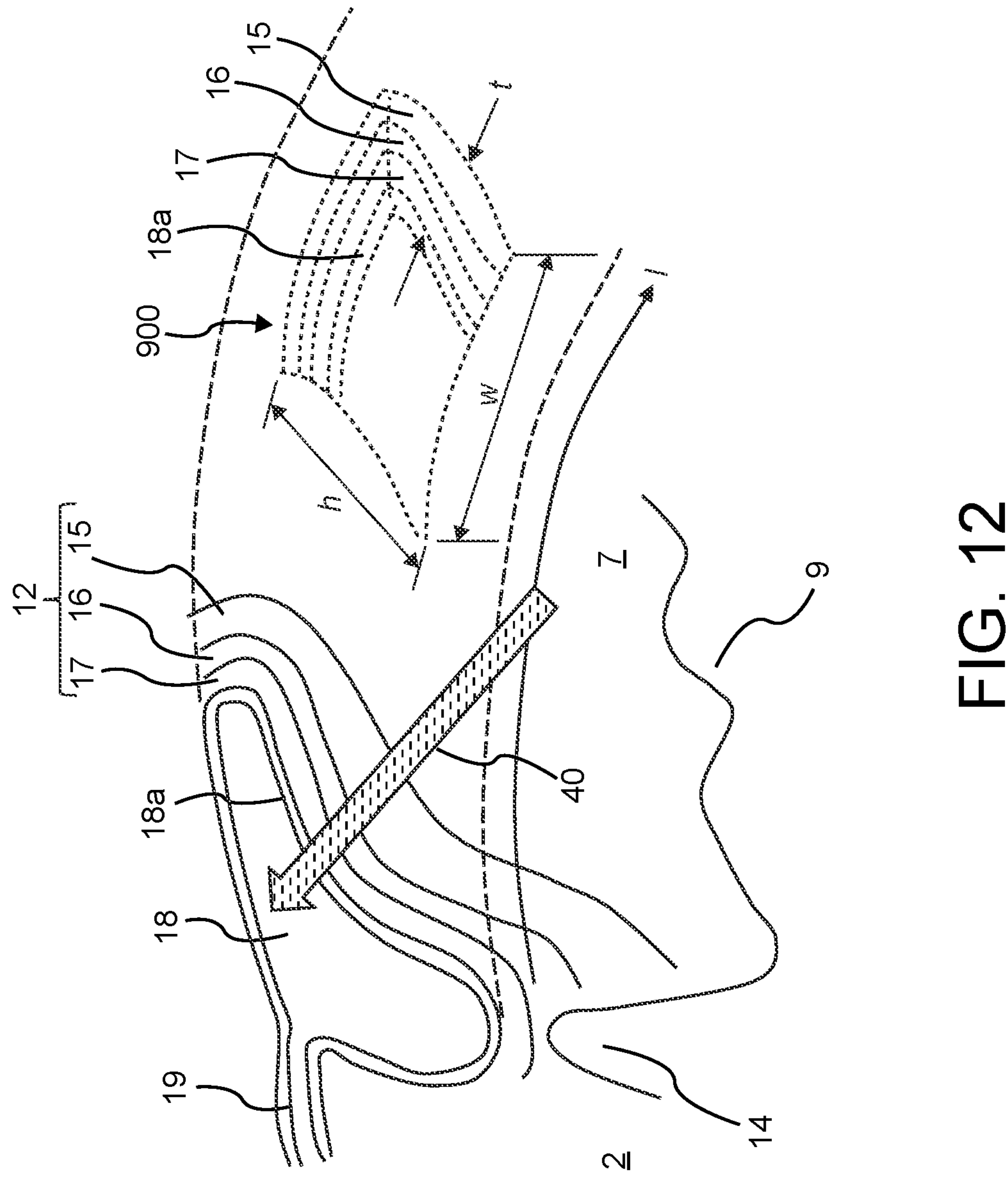
FIG. 12 is a three-dimensional schematic illustration of anatomical structures in the irido-corneal angle, including the trabecular meshwork, Schlemm's canal, a collector channel branching from the Schlemm's canal, and a surgical volume of ocular tissue to be treated by an integrated surgical system.

FIG. 12 is a three-dimensional schematic illustration of anatomical structures of the eye relevant to the surgical treatment enabled by the integrated surgical system 1000. To reduce the IOP, laser treatment targets ocular tissues that affect the trabecular outflow pathway 40. These ocular tissues may include the trabecular meshwork 12, the scleral spur 14, the Schlemm's canal 18, and the collector channels 19. The trabecular meshwork 12 has three layers, the uveal 15, the corneoscleral meshwork 16, and the juxtacanalicular tissue 17. These layers are porous and permeable to aqueous, with the uveal 15 being the most porous and permeable, followed by the corneoscleral meshwork 16. The least porous and least permeable layer of the trabecular meshwork 12 is the juxtacanalicular tissue 17. The inner wall 18*a* of the Schlemm's canal 18, which is also porous and permeable to aqueous, has characteristics similar to the juxtacanalicular tissue 17.

Figure 13:
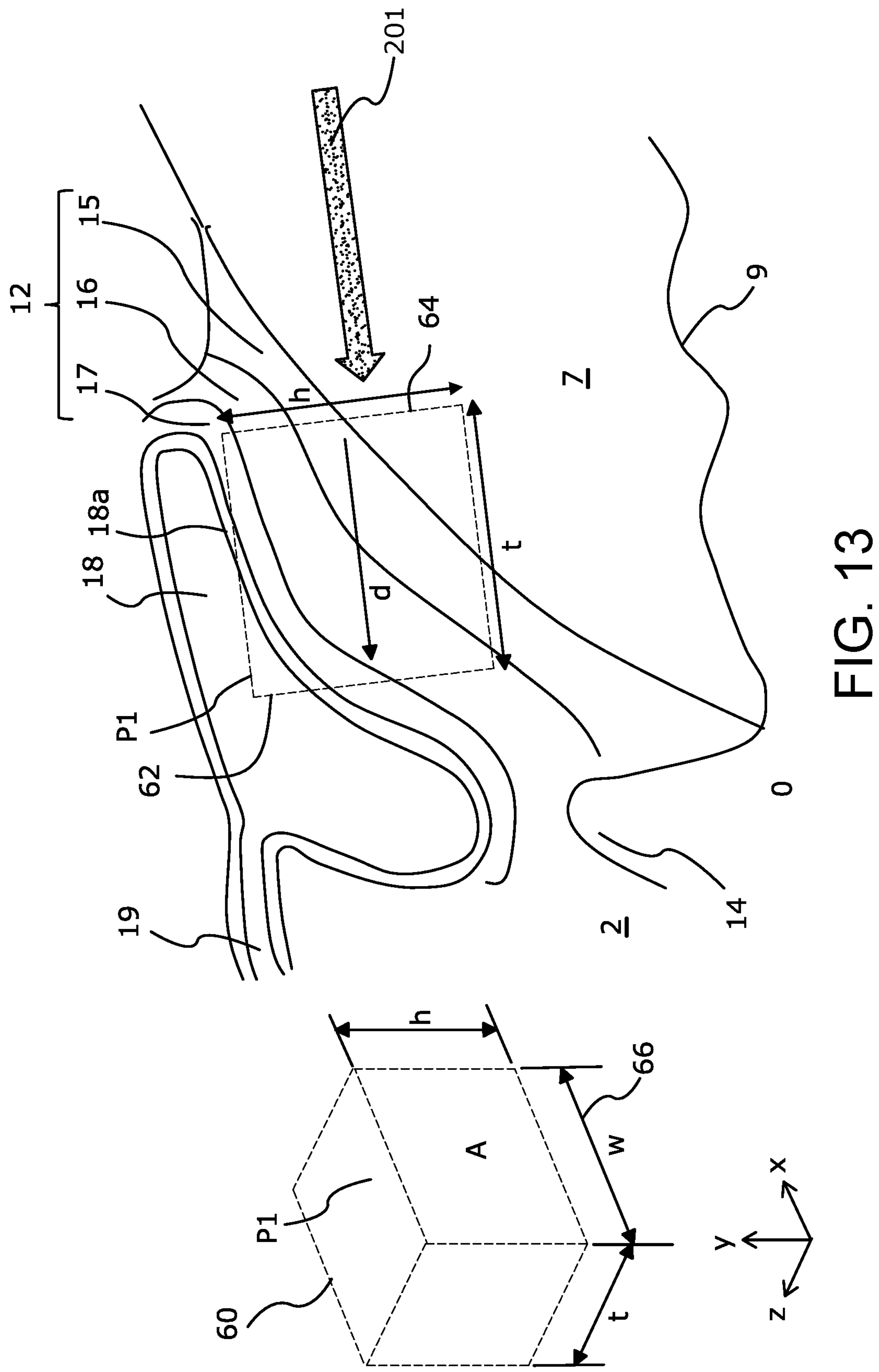
FIG. 13 is a two-dimensional schematic illustrations of anatomical structures in the irido-corneal angle and a three-dimensional laser treatment pattern to be applied by an integrated surgical system to affect a surgical volume of ocular tissue between the Schlemm's canal and the anterior chamber as shown in FIG. 12.

FIG. 13 includes three-dimensional illustrations of a treatment pattern P1 to be applied by the integrated surgical system 1000 to affect the surgical volume 900 of ocular tissue shown in FIG. 12, and a two-dimensional schematic illustration of the treatment pattern P1 overlaying anatomical structures to be treated. FIG. 13 is a three-dimensional schematic illustration of the anatomical structures of the eye including an opening 902 through the trabecular meshwork 12 that results from the application of the laser treatment pattern of FIG. 13. The opening 902 may also be referred to as a channel or aperture. The opening 902 provides and outflow pathway 40 that reduces the flow resistance in the ocular tissue to increase aqueous flow from the anterior chamber 7 into the Schlemm's canal 18 and thereby reduce the IOP of the eye.

Surgical treatments reduce outflow pathway resistance while minimizing ocular tissue modification through design and selection of laser treatment patterns. A treatment pattern is considered to define a collection of a laser-tissue interaction volumes, referred to herein as cells. The size of a cell is determined by the extent of the influence of the laser-tissue interaction. When the laser spots, or cells, are spaced close along a line, the laser creates a narrow, microscopic channel. A wider channel can be created by closely spacing a multitude of laser spots within the cross section of the channel. The arrangement of the cells may resemble the arrangement of atoms in a crystal structure.

With reference to FIG. 13, a treatment pattern P1 may be in the form of a cubic structure that encompasses individual cells arranged in regularly spaced rows, columns and sheets or layers. The treatment pattern P1 may be characterized by x, y, z dimensions, with x, y, z coordinates of the cells being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser or a three-dimensional model of ocular fluid to be affected by a laser.

A treatment pattern P1 is typically defined by a set of surgical parameters. The surgical parameters may include one or more of a treatment area A that represents a surface area or layer of ocular tissue through which the laser will travel. The treatment area A is determined by the treatment height, h, and the lateral extent of the treatment, w. A treatment thickness t that represents the level to which the laser will cut into the ocular tissue from the distal extent or border of the treatment volume at or near Schlemm's canal 18 to the proximal extent or border at or near the surface of the trabecular meshwork 12. Thus, a laser applied in accordance with a treatment pattern may affect or produce a surgical volume that resembles the three-dimensional model of the treatment pattern, or may affect fluid located in an interior of an eye structure resembled by the three-dimensional model.

Additional surgical parameters define the placement of the surgical volume or affected volume within the eye. For example, with reference to FIGS. 12 and 13, placement parameters may include one or more of a location 1 that represents where the treatment is to occur relative to the circumferential angle of the eye, and a treatment depth d that represents a position of the three-dimensional model of ocular tissue or ocular fluid within the eye relative to a reference eye structure. In the following, the treatment depth d is shown and described relative to the region where the anterior chamber 7 meets the trabecular meshwork 12. Together, the treatment pattern and the placement parameters define a treatment plan.

A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

With reference to FIGS. 12 and 13, a surgical volume 900 of ocular tissue to be treated is identified by the integrated surgical system 1000 and a treatment pattern P1 corresponding to the surgical volume is designed by the integrated surgical system. Alternatively, the treatment pattern P1 may be designed first, and then an appropriate surgical volume 900 for applying the treatment pattern may be identified. The surgical volume 900 of ocular tissue may comprise portions of the trabecular meshwork 12 and the Schlemm's canal 18. For example, the surgical volume 900 of ocular tissue shown in FIG. 14 includes portions of the uveal 15, the corneoscleral meshwork 16, the juxtacanalicular tissue 17, and the inner wall 18*a* of the Schlemm's canal 18. The treatment pattern P1 defines a laser scanning procedure whereby a laser is focused at different depth locations in ocular tissue and then scanned in multiple directions to affect a three-dimensional volume of tissue comprising multiple sheets or layers of affected tissue.

Figure 14:
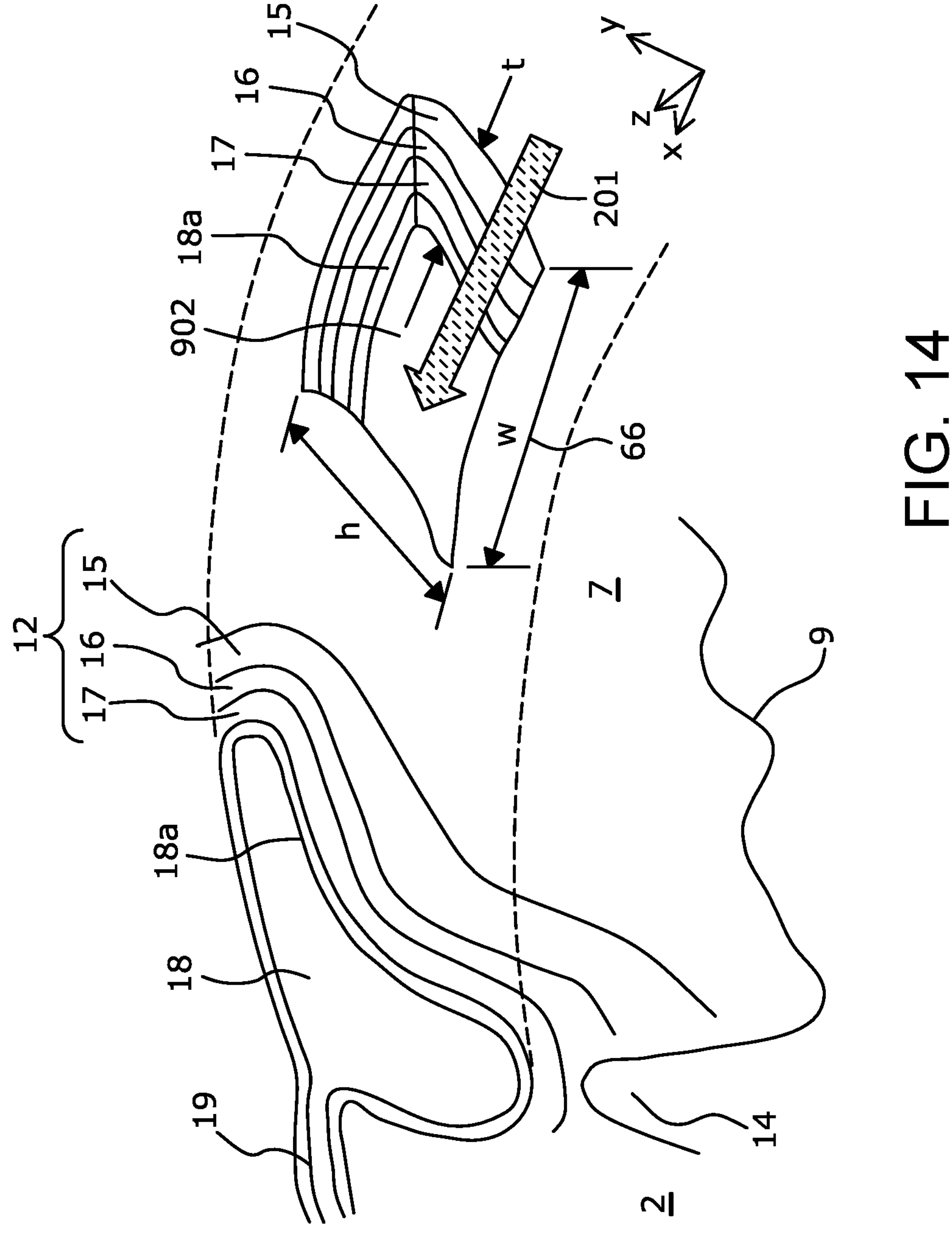
FIG. 14 is a three-dimensional schematic illustration of FIG. 12 subsequent to treatment of the surgical volume of ocular tissue by a laser based on the laser treatment pattern of FIG. 13 that forms an opening between the Schlemm's canal and the anterior chamber.

With reference to FIGS. 13 and 14, during a laser scanning procedure, a surgical laser beam 201 may scan ocular tissue in accordance with the treatment pattern P1 to form an opening 902 that extends from the anterior chamber 7, through each of the uveal 15, the corneoscleral meshwork 16, the juxtacanalicular tissue 17 of the trabecular meshwork 12, and the inner wall 18*a* of the Schlemm's canal 18. While the example opening 902 in FIG. 16 is depicted as a continuous, single lumen defining a fluid pathway, the opening may be defined an arrangement of adjacent pores forming a sponge like structure defining a fluid pathway or a combination thereof. While the example opening 902 in FIG. 14 is in the shape of a cube, the opening may have other geometric shapes.

The movement of the laser as it scans to affect the surgical volume 900 follows the treatment pattern P1, which is defined by a set of surgical parameters that include a treatment area A and a thickness t. The treatment area A is defined by a width w and a height h. The width may be defined in terms of a measure around the circumferential angle. For example, the width w may be defined in terms of an angle, e.g., 90 degrees, around the circumferential angle.

Referring to FIGS. 13, an initial placement of the laser focus within the eye is defined by a set of placement parameters, including a depth d and a location l. The location l defines a point around the circumferential angle of the eye at which laser treatment will begin, while the depth d defines a point between the anterior chamber 7 and the Schlemm's canal 18 where the laser treatment begins or ends. The depth d is measured relative to the region where the anterior chamber 7 meets the trabecular meshwork 12. Thus, a first point that is closer to the Schlemm's canal 18 side of the trabecular meshwork 12 may be described as being deeper than a second point that is closer to the anterior chamber 7 side of the trabecular meshwork 12. Alternatively, the second point may be described as being shallower than the first point.

With reference to FIG. 14, the opening 902 resulting from laser application of the treatment pattern P1 resembles the surgical volume 900 and is characterized by an area A and thickness t similar to those of the surgical volume and the treatment pattern. The thickness t of the resulting opening 902 extends from the anterior chamber 7 and through the inner wall 18*a* of the Schlemm's canal 18, while the area A defines the cross-section size of the opening 902.

During a laser scanning procedure, a laser focus is moved to different depths d in ocular tissue and then scanned in two lateral dimensions or directions as defined by a treatment pattern P1 to affect a three-dimensional surgical volume 900 of ocular tissue comprising multiple sheets or layers of affected tissue. The two lateral dimensions are generally orthogonal to the axis of movement of the laser focus. With reference to FIG. 14, the movement of a laser focus during laser scanning is described herein with reference to x, y, and z directions or axes, wherein: 1) movement of the laser focus to different depths d through the thickness t of treatment pattern P1 or the surgical volume 900 of tissue corresponds to movement of the focus along the z axis, 2) movement of the laser focus in two dimensions or directions orthogonal to the z axis corresponds to movement of the laser focus along the width w of the treatment pattern P1 or the surgical volume 900 of tissue in the x direction, and movement of the laser focus along the height h of the treatment pattern P1 or the surgical volume 900 of tissue in the y direction.

As used herein scanning of the laser focus generally corresponds to a raster type movement of the laser focus in the x direction, the y direction, and the z direction. The laser focus may be located at a point in the z direction and then raster scanned in two dimensions or directions, in the x direction and the y direction. The focal point of the laser in the z direction may be referred to as a depth d within the treatment pattern P1 or the surgical volume 900 of tissue. The two-direction raster scanning of the laser focus defines a layer of laser scanning, which in turn produces a layer of laser-affected tissue.

During laser scanning, pulse shots of a laser are delivered to tissue within the volume of ocular tissue corresponding to the treatment pattern P1. Because the laser interaction volume is small, on the order of a few micrometers (m), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Figures 15A, 15B:
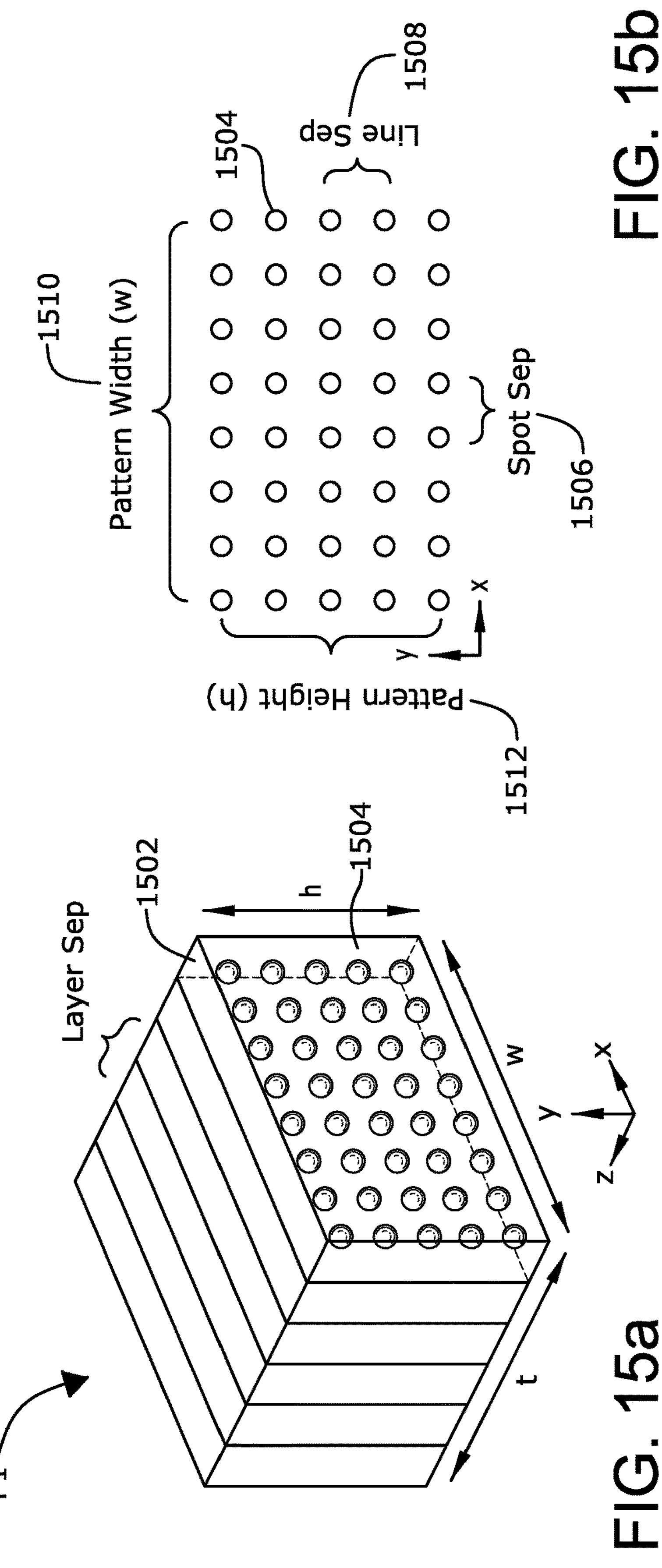
FIG. 15*a* is a schematic illustration of a three-dimensional laser treatment pattern formed by a number of stacked two-dimensional treatment planes or layers.
FIG. 15*b* is a schematic illustration of a two-dimensional treatment layer defined by an array of spots.

With reference to FIGS. 15*a* and 15*b*, a 3D treatment pattern P1 may be defined by a number of 2D treatment layers 1502 or treatment planes that are stacked to form a 3D treatment pattern characterized by a width w, height h, and depth or thickness t. Each individual treatment layer 1502 is in turn characterized by a pattern height h (equal to the height h of the 3D treatment pattern P1) and a pattern width w (equal to the width w of the 3D treatment pattern P1) and comprises an array of spots 1504 spaced apart to establish or fit within the height and width. The pattern width w corresponds to a distance along the circumference of the corneal angle parallel to the trabecular meshwork. This direction is also known as the circumferential direction. The pattern height h corresponds to a distance transverse to the circumference of the corneal angle perpendicular to the trabecular meshwork. This direction is also known as the azimuthal direction.

Each spot 1504 in the treatment pattern P1 corresponds to a site within a target volume of ocular tissue where optical energy is applied at a laser focus to create a micro-photodisruption site. With reference to FIG. 15*b*, each spot 1504 in a treatment layer 1502 is separated from a neighboring spot by programmable distances called spot separation (Spot Sep 1506) and a line separation (Line Sep 1508). A treatment layer 1502 is completed with the programmed pattern width w 1510 and pattern height h 1512 is achieved. Each treatment layer 1502 in the 3D treatment pattern P1 is separated from a neighboring layer by a layer separation (Layer Sep).

A treatment pattern P1 may be defined by a set of programmable parameters, such as shown in Table 1.

TABLE 1

| Parameter | Minimum | Maximum |
|---|---|---|
| width w | 10 μm | 2000 μm |
| height h | 10 μm | 2000 μm |
| depth/thickness t | 10 μm | 4000 μm |
| Spot Sep | 2 μm | 40 μm |
| Line Sep | 2 μm | 40 μm |
| Layer Sep | 2 μm | 200 μm |
| pulse energy | 0 μJ | 35 μJ |

Other, non-rectangular and more irregular treatment patterns can also be programmed and created in the tissue. These irregular patterns can still be decomposed to spots, lines, and layers and their extent characterized by width, height, and depth. Examples of irregular treatment patterns are described in U.S. Patent Application Publication No. 2021/0307964, entitled Method, System, and Apparatus for Generating Three-Dimensional Treatment Patterns for Laser Surgery of Glaucoma, the disclosure of which is hereby incorporated by reference.

In one example treatment pattern P1, the parameters are:

width=750 μm height=250 μm depth=350 μm spot separation=10 μm line separation=10 μm layer separation=10 μm During laser treatment, each treatment layer 1502 is individually created by scanning the laser focus in two dimensions, e.g., width and height, or z and y, to the various spots 1504 defining the layer, while the focus is fixed at the third dimension, e.g., depth or Z. Once a treatment layer 1502 is created, the focus is moved in the depth or z direction and the next treatment layer in the stack is created. This process is repeated until all treatment layers 1502 in the 3D treatment pattern P1 are created. Details on this type of scanning are disclosed in U.S. Patent Application Publication No. 2021/0220176, the entire disclosure of which is hereby incorporated by reference.

In another treatment, instead of creating a treatment pattern P1 one treatment layer 1502 at a time, the focus of the laser beam 201 is scanned in three dimensions. For example, while the laser focus is being moved transversely through a height and/or width, e.g., in the x and/or y direction, the laser focus is also oscillated back and forth axially through a depth, e.g., in the z direction. The treatment pattern P1 characterized by such scanning of the laser focus may be referred to as a "clearing pattern." Oscillation of the laser focus through the depth in the z direction occurs simultaneous with transverse movement of the laser focus in the x and y directions. An example of scanning a laser in accordance with a clearing pattern is also disclosed in U.S. Patent Application Publication No. 2021/0220176.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An integrated surgical system for accessing one of a plurality of target volumes of ocular tissue in an eye having an optical axis, the system comprising:

- a first optical transmission subsystem optically coupled to receive a first light beam;
- an optics assembly having an optical axis, the optics assembly configured to couple to the eye to align its optical axis with the optical axis of the eye, the optics assembly optically coupled with the first optical transmission subsystem to receive the first light beam along one of a plurality of first input axes and to direct the first light beam to a corresponding one of a plurality of first output axes aligned with a corresponding one of the plurality of target volumes of ocular tissue in the eye;
- a control system configured to control the first optical transmission subsystem to direct the first light beam into alignment with a select one of the plurality of first input axes; and
- a housing configured to rotate about the optical axis of the optics assembly, wherein:
- the optics assembly comprises an exit lens having a convex surface to which the first light beam is incident, a concave surface opposite the convex surface, a side region that extends between the convex surface and the concave surface, and a reflecting surface associated with the side region, which receives the first light beam and redirects the first light beam through the concave surface along the corresponding first output axis,
- one or more components of the first optical transmission subsystem are mechanically coupled to the housing,
- the optics assembly is asymmetric and is mechanically coupled to the housing, and
- the control system is configured to rotate the housing about the optical axis of the optics assembly such that the one or more components of the optics assembly rotates about the optical axis of the optics assembly and the one or more components of the first optical transmission subsystem revolve around the optical axis of the optics assembly.

2. The integrated surgical system of claim 1, wherein the first optical transmission subsystem comprises a means for aligning the first light beam with the one of the plurality of first input axes.

3. The integrated surgical system of claim 2, wherein the means for aligning the first light beam comprises at least one adjustable reflecting surface optically aligned to receive the first light beam along an angle of incidence and to reflect the first light beam at an angle of reflection into alignment with the corresponding one of the plurality of first input axes.

4. The integrated surgical system of claim 3, wherein the adjustable reflecting surface comprises an actuated flip mirror or an actuated angular deflector.

5. The integrated surgical system of claim 1, wherein the first optical transmission subsystem is optically coupled to receive a plurality of different types of light beams and comprises a means for colinearly combining the plurality of different types of light beams into the first light beam.

6. The integrated surgical system of claim 5, wherein the means for colinearly combining the plurality of different types of light beams into the first light beam comprises at least one beam splitter and fiber-optic equivalents thereof.

7. The integrated surgical system of claim 6, wherein the at least one beam splitter comprises at least one polarization beam splitter and fiber-optic equivalents thereof.

8. The integrated surgical system of claim 6, wherein the at least one beam splitter comprises at least one dichroic or multiple wavelengths beam splitter and fiber-optic equivalents thereof.

9. The integrated surgical system of claim 1, wherein the first optical transmission subsystem comprises a focusing objective and the control system is configured to control the focusing objective to focus the first light beam at the corresponding one of the plurality of target volumes of ocular tissue.

10. The integrated surgical system of claim 1, wherein the first light beam is a laser beam.

11. The integrated surgical system of claim 1, further comprising a laser source configured to output the first light beam.

12. The integrated surgical system of claim 1, wherein the first light beam is a colinear beam comprising a laser beam and at least one of an OCT beam, a visual observation beam, and a pair of dual aiming beams.

13. The integrated surgical system of claim 1, further comprising a second optical transmission subsystem optically coupled to receive a second light beam, wherein:

- the optics assembly is optically coupled with the second optical transmission subsystem to receive the second light beam along one of a plurality of second input axes and to direct the second light beam to a corresponding one of a plurality of second output axes aligned with a corresponding one of the plurality of target volumes of ocular tissue in the eye; and
- the control system is configured to control the second optical transmission subsystem to direct the second light beam into alignment with a select one of the plurality of second input axes.

14. The integrated surgical system of claim 13, wherein the second optical transmission subsystem comprises a means for aligning the second light beam with the one of the plurality of second input axes.

15. The integrated surgical system of claim 13, wherein the second optical transmission subsystem is optically coupled to receive a plurality of different types of light beams and comprises a means for combining the plurality of different types of light beams into the second light beam.

16. The integrated surgical system of claim 13, wherein the second light beam comprising at least one of a laser beam, an OCT beam, a visual observation beam, and a pair of dual aiming beams.

17. The integrated surgical system of claim 13, wherein the second optical transmission subsystem comprises a focusing objective and the control system is configured to control the focusing objective to focus the second light beam at the corresponding one of the plurality of target volumes of ocular tissue.

18. The integrated surgical system of claim 13, wherein one or more components of the second optical transmission subsystem is mechanically coupled to a structure configured to rotate a portion of the second optical transmission subsystem about the optical axis of the optics assembly.

19. The integrated surgical system of claim 1, wherein the plurality of target volumes of ocular tissue comprises an irido-corneal angle, a cornea, a lens capsule, and a crystalline lens.

20. A method of accessing one of a plurality of target volumes of ocular tissue in an eye having an optical axis, the method comprising:

receiving a first light beam at a first optical transmission subsystem;

directing, by the first optical transmission subsystem, the first light beam to a select one of a plurality of first inputs axes of an optics assembly coupled to the eye, wherein the optics assembly has an optical axis and is configured to couple to the eye to align its optical axis with the optical axis of the eye;

directing, by the optics assembly, the first light beam along the select one of the plurality of first inputs axes to a corresponding one of a plurality of first output axes of the optics assembly aligned with a corresponding one of the plurality of target volumes of ocular tissue in the eye; and rotating a housing about the optical axis of the optics assembly such that one or more components of the optics assembly rotate about the optical axis of the optics assembly and one or more components of the first optical transmission subsystem revolve around the optical axis of the optics assembly, wherein:

the optics assembly comprises an exit lens having a convex surface to which the first light beam is incident, a concave surface opposite the convex surface, a side region that extends between the convex surface and the concave surface, and a reflecting surface associated with the side region, which receives the first light beam and redirects the first light beam through the concave surface along the corresponding first output axis, the one or more components of the first optical transmission subsystem are mechanically coupled to the housing, and the optics assembly is asymmetric and is mechanically coupled to the housing.

21. The method of claim 20, wherein directing, by the first optical transmission subsystem, the first light beam to a select one of a plurality of first inputs axes of an optics assembly comprises controlling a position of an alignment mechanism of the first optical transmission subsystem.

22. The method of claim 20, wherein the first light beam is one of a laser beam, an OCT beam, a visual observation beam, and dual aiming beams.

23. The method of claim 20, wherein the first light beam is a colinear combination of two or more of a laser beam, an OCT beam, a visual observation beam, and dual aiming beams.

24. The method of claim 20, further comprising:

receiving a second light beam at a second optical transmission subsystem;

directing, by the first optical transmission subsystem, the second light beam to a select one of a plurality of second inputs axes of the optics assembly coupled to the eye; and directing, by the optics assembly, the second light beam along the select one of the plurality of second inputs axes to a corresponding one of a plurality of second output axes of the optics assembly aligned with a corresponding one of the plurality of target volumes of ocular tissue in the eye.

25. The method of claim 24, wherein directing, by the second optical transmission subsystem, the second light beam to a select one of a plurality of second inputs axes of the optics assembly comprises controlling a position of an alignment mechanism of the second optical transmission subsystem.

26. The method of claim 24, wherein receiving the first light beam and receiving the second light beam occur simultaneously.

27. The method of claim 24, wherein the target volume of ocular tissue aligned with the first output axes of the optics assembly and the target volume of ocular tissue aligned with the second output axes of the optics assembly are the same target volume.

28. The method of claim 24, wherein the target volume of ocular tissue aligned with the first output axes of the optics assembly and the target volume of ocular tissue aligned with the second output axes of the optics assembly are different target volumes.

29. An integrated surgical system for accessing one of a plurality of target volumes of ocular tissue in an eye having an optical axis, the system comprising:

a first optical transmission subsystem optically coupled to receive a first light beam;

an optics assembly having an optical axis, the optics assembly configured to couple to the eye to align its optical axis with the optical axis of the eye, the optics assembly optically coupled with the first optical transmission subsystem to receive the first light beam along one of a plurality of first input axes and to direct the first light beam to a corresponding one of a plurality of first output axes aligned with a corresponding one of the plurality of target volumes of ocular tissue in the eye;

a control system configured to control the first optical transmission subsystem to direct the first light beam into alignment with a select one of the plurality of first input axes; and a housing having a non-rotatable portion and a rotatable portion configured to rotate about the optical axis of the optics assembly, wherein:

the optics assembly comprises an exit lens having a convex surface to which the first light beam is incident, a concave surface opposite the convex surface, a side region that extends between the convex surface and the concave surface, and a reflecting surface associated with the side region, which receives the first light beam and redirects the first light beam through the concave surface along the corresponding first output axis, one or more components of the first optical transmission subsystem are mechanically coupled to the rotatable portion, the optics assembly is symmetric and is mechanically coupled to the non-rotatable portion, and the control system is configured to rotate the rotatable portion of the housing about the optical axis of the optics assembly such that the one or more components of the first optical transmission subsystem revolve around the optical axis of the optics assembly.

30. The integrated surgical system of claim 29, wherein the first optical transmission subsystem comprises a means for aligning the first light beam with the one of the plurality of first input axes.

31. The integrated surgical system of claim 30, wherein the means for aligning the first light beam comprises at least one adjustable reflecting surface optically aligned to receive the first light beam along an angle of incidence and to reflect the first light beam at an angle of reflection into alignment with the corresponding one of the plurality of first input axes.

32. The integrated surgical system of claim 31, wherein the adjustable reflecting surface comprises an actuated flip mirror or an actuated angular deflector.

33. The integrated surgical system of claim 29, wherein the first optical transmission subsystem is optically coupled to receive a plurality of different types of light beams and comprises a means for colinearly combining the plurality of different types of light beams into the first light beam.

34. The integrated surgical system of claim 33, wherein the means for colinearly combining the plurality of different types of light beams into the first light beam comprises at least one beam splitter and fiber-optic equivalents thereof.

35. The integrated surgical system of claim 34, wherein the at least one beam splitter comprises at least one polarization beam splitter and fiber-optic equivalents thereof.

36. The integrated surgical system of claim 34, wherein the at least one beam splitter comprises at least one dichroic or multiple wavelengths beam splitter and fiber-optic equivalents thereof.

37. The integrated surgical system of claim 29, wherein the first optical transmission subsystem comprises a focusing objective and the control system is configured to control the focusing objective to focus the first light beam at the corresponding one of the plurality of target volumes of ocular tissue.

38. The integrated surgical system of claim 29, wherein the first light beam is a laser beam.

39. The integrated surgical system of claim 29, further comprising a laser source configured to output the first light beam.

40. The integrated surgical system of claim 29, wherein the first light beam is a colinear beam comprising a laser beam and at least one of an OCT beam, a visual observation beam, and a pair of dual aiming beams.

41. The integrated surgical system of claim 29, further comprising a second optical transmission subsystem optically coupled to receive a second light beam, wherein:

the optics assembly is optically coupled with the second optical transmission subsystem to receive the second light beam along one of a plurality of second input axes and to direct the second light beam to a corresponding one of a plurality of second output axes aligned with a corresponding one of the plurality of target volumes of ocular tissue in the eye; and the control system is configured to control the second optical transmission subsystem to direct the second light beam into alignment with a select one of the plurality of second input axes.

42. The integrated surgical system of claim 41, wherein the second optical transmission subsystem comprises a means for aligning the second light beam with the one of the plurality of second input axes.

43. The integrated surgical system of claim 41, wherein the second optical transmission subsystem is optically coupled to receive a plurality of different types of light beams and comprises a means for combining the plurality of different types of light beams into the second light beam.

44. The integrated surgical system of claim 41, wherein the second light beam comprising at least one of a laser beam, an OCT beam, a visual observation beam, and a pair of dual aiming beams.

45. The integrated surgical system of claim 41, wherein the second optical transmission subsystem comprises a focusing objective and the control system is configured to control the focusing objective to focus the second light beam at the corresponding one of the plurality of target volumes of ocular tissue.

46. The integrated surgical system of claim 41, wherein one or more components of the second optical transmission subsystem is mechanically coupled to a structure configured to rotate a portion of the second optical transmission subsystem about the optical axis of the optics assembly.

47. The integrated surgical system of claim 29, wherein the plurality of target volumes of ocular tissue comprises an irido-corneal angle, a cornea, a lens capsule, and a crystalline lens.

48. A method of accessing one of a plurality of target volumes of ocular tissue in an eye having an optical axis, the method comprising:

receiving a first light beam at a first optical transmission subsystem;

directing, by the first optical transmission subsystem, the first light beam to a select one of a plurality of first inputs axes of an optics assembly coupled to the eye, wherein the optics assembly has an optical axis and is configured to couple to the eye to align its optical axis with the optical axis of the eye;

directing, by the optics assembly, the first light beam along the select one of the plurality of first inputs axes to a corresponding one of a plurality of first output axes of the optics assembly aligned with a corresponding one of the plurality of target volumes of ocular tissue in the eye; and rotating a rotatable portion of a housing about the optical axis of the optics assembly such that one or more components of the first optical transmission subsystem revolve around the optical axis of the optics assembly, wherein:

the optics assembly comprises an exit lens having a convex surface to which the first light beam is incident, a concave surface opposite the convex surface, a side region that extends between the convex surface and the concave surface, and a reflecting surface associated with the side region, which receives the first light beam and redirects the first light beam through the concave surface along the corresponding first output axis, the one or more components of the first optical transmission subsystem are mechanically coupled to the rotatable portion, and the optics assembly is symmetric and is mechanically coupled to a non-rotatable portion of the housing.

* * * * *